(12) United States Patent
Tallarida et al.

(10) Patent No.: US 6,989,016 B2
(45) Date of Patent: Jan. 24, 2006

(54) VASCULAR SUCTION CANNULA, DILATOR AND SURGICAL STAPLER

(75) Inventors: Steven J. Tallarida, Mansfield, MA (US); Mark Ettlinger, Lexington, MA (US)

(73) Assignee: Medtronic Angiolink, Inc., Santa Rosa, CA (US)

( * ) Notice: Subject to any disclaimer, the term of this patent is extended or adjusted under 35 U.S.C. 154(b) by 44 days.

(21) Appl. No.: 10/689,358

(22) Filed: Oct. 20, 2003

(65) Prior Publication Data

US 2004/0082906 A1    Apr. 29, 2004

Related U.S. Application Data

(63) Continuation of application No. 09/486,185, filed as application No. PCT/US99/16476 on Jul. 21, 1999, now abandoned.

(60) Provisional application No. 60/093,701, filed on Jul. 22, 1998.

(51) Int. Cl.
*A61B 17/10*    (2006.01)

(52) U.S. Cl. .................. 606/142; 227/175.1; 227/179.1
(58) Field of Classification Search ................ 606/139, 606/142, 143; 227/175.1, 179.1, 181.1, 176.1, 227/178.1
See application file for complete search history.

(56) References Cited

U.S. PATENT DOCUMENTS 2,568,566 A    9/1951    Sokolik ....................... 604/35

(Continued)

FOREIGN PATENT DOCUMENTS

EP    0455 626 B1    11/1991

OTHER PUBLICATIONS

Canadian Office Action for Canadian Application No. 2,339,060 mailed on Jul. 26, 2004, 3 pgs.

*Primary Examiner*—Sharon Kennedy

(57) ABSTRACT

A suction cannula, dilator, stapler and staple are provided herein. The suction cannula is concentrically aligned with a puncture site (e.g., puncture in an artery or vein) and provides vacuum about the periphery of the puncture site so that the puncture hole is always located during a medical procedure, and to thereby permit a surgeon to quickly and efficiently close the puncture using, for example, a stapling device. In the preferred embodiment the suction cannula has a tube-in-tube construction having an inner tube and an outer tube where a vacuum can be applied between the tubes. The dilator (and suction cannula) centers around a guide wire (that is already in place within the venous structure) and follows the path of the guide wire to the puncture site. Preferably, the dilator has a tapered tip on the distal end that enters a hole made in the vein or artery. A blood indicator is provided on the proximal end to provide visual feedback when the surgeon is in the artery (i.e., pulsating blood indicates that the tip of the dilator is in the artery). Also preferably, the dilator includes a tapered tip on the distal end that is radially collapsible so that the dilator can be withdrawn from the artery and the suction cannula is thereby permitted to advance over the dilator to the artery wall. The stapler is provided which holds a multi-pronged staple on a shaft at the distal end. The stapler is constructed to slide into the suction cannula (i.e., the inner tube of the cannula) to approach the puncture in the artery, to permit the stapling of the artery. Preferably, the distal end of the stapler includes a T-flange that holds a staple and a crimping mechanism that crimps the staple into the artery, thereby sealing the puncture. The T-flange permits the staple to be held and inserted into the artery wall. An oval hub on the T-flange is provided that mates with an oval hole in the center of the staple. To hold a staple, a staple is placed on the hub and rotated 90 degrees, thereby affixing the staple to the stapler. Once the staple is crimped onto the artery wall, the shaft can be rotated 90 degrees, thereby aligning the oval hub and the oval hole, so that the stapler can be removed. Preferably, the staple includes a plurality of prongs that are inserted into the vascular wall.

10 Claims, 21 Drawing Sheets

U.S. PATENT DOCUMENTS

| | | | |
|---|---|---|---|
| 4,441,497 A | 4/1984 | Paudler | 128/339 |
| 4,469,101 A | 9/1984 | Coleman et al. | 128/334 |
| 4,648,871 A | 3/1987 | Jacob | 604/149 |
| 4,836,205 A | 6/1989 | Barrett | 128/340 |
| 4,932,962 A | 6/1990 | Yoon et al. | 606/224 |
| 4,950,285 A | 8/1990 | Wilk | 606/232 |
| 4,990,153 A | 2/1991 | Richards | 606/148 |
| 5,029,580 A | 7/1991 | Radford et al. | 128/207.14 |
| 5,037,433 A | 8/1991 | Wilk et al. | 606/139 |
| 5,053,047 A | 10/1991 | Yoon | 606/223 |
| 5,074,874 A | 12/1991 | Yoon, Inbae et al. | 606/224 |
| 5,104,394 A | 4/1992 | Knoepfler | 606/143 |
| 5,123,913 A | 6/1992 | Wilk et al. | 606/232 |
| 5,222,976 A | 6/1993 | Yoon | 606/223 |
| 5,234,445 A | 8/1993 | Walker et al. | 606/148 |
| 5,234,447 A | 8/1993 | Kaster et al. | 606/153 |
| 5,250,053 A | 10/1993 | Snyder | 606/145 |
| 5,279,311 A | 1/1994 | Snyder | 128/898 |
| 5,281,237 A | 1/1994 | Gimpelson | 606/144 |
| 5,282,809 A | 2/1994 | Kammerer et al. | 606/148 |
| 5,320,629 A | 6/1994 | Noda et al. | 606/139 |
| 5,330,491 A | 7/1994 | Walker et al. | 606/148 |
| 5,334,198 A | 8/1994 | Hart et al. | 606/52 |
| 5,342,374 A | 8/1994 | Wan et al. | 606/148 |
| 5,364,407 A | 11/1994 | Poll | 606/139 |
| 5,364,408 A | 11/1994 | Gordon | 606/144 |
| 5,370,610 A | 12/1994 | Reynolds | 604/43 |
| 5,374,275 A | 12/1994 | Bradley et al. | 606/144 |
| 5,391,173 A | 2/1995 | Wilk | 606/144 |
| 5,403,333 A | 4/1995 | Kaster et al. | 606/151 |
| 5,405,354 A | 4/1995 | Sarrett | 606/148 |
| 5,417,699 A | 5/1995 | Klein et al. | 606/144 |
| 5,423,833 A | 6/1995 | Zauza | 606/139 |
| 5,439,467 A | 8/1995 | Benderev et al. | 606/139 |
| 5,460,613 A | 10/1995 | Ulrich et al. | 604/118 |
| 5,462,561 A | 10/1995 | Voda | 606/144 |
| 5,462,562 A | 10/1995 | Elkus | 606/148 |
| 5,468,251 A | 11/1995 | Buelna | 606/223 |
| 5,490,503 A | 2/1996 | Hollister | 128/205.12 |
| 5,496,335 A | 3/1996 | Thomason et al. | 606/148 |
| 5,501,690 A | 3/1996 | Measamer et al. | 606/146 |
| 5,507,758 A | 4/1996 | Thomason et al. | 606/148 |
| 5,522,821 A | 6/1996 | Brown | 606/148 |
| 5,544,664 A | 8/1996 | Benderev et al. | 128/898 |
| 5,545,170 A | 8/1996 | Hart | 606/148 |
| 5,554,162 A | 9/1996 | DeLange | 606/153 |
| 5,569,269 A | 10/1996 | Hart et al. | 606/144 |
| 5,569,271 A | 10/1996 | Hoel | 606/148 |
| 5,571,119 A | 11/1996 | Atala | 606/146 |
| 5,573,540 A | 11/1996 | Yoon | 606/139 |
| 5,618,290 A | 4/1997 | Toy et al. | 606/139 |
| 5,695,504 A * | 12/1997 | Gifford et al. | 606/153 |
| 5,709,335 A | 1/1998 | Heck | 227/176.1 |
| 5,713,849 A | 2/1998 | Bosma et al. | 604/28 |
| 5,715,815 A | 2/1998 | Lorenzen et al. | 128/207.14 |
| 6,001,078 A | 12/1999 | Reekers | 604/43 |
| 6,428,498 B2 | 8/2002 | Uflacker | 604/22 |

\* cited by examiner

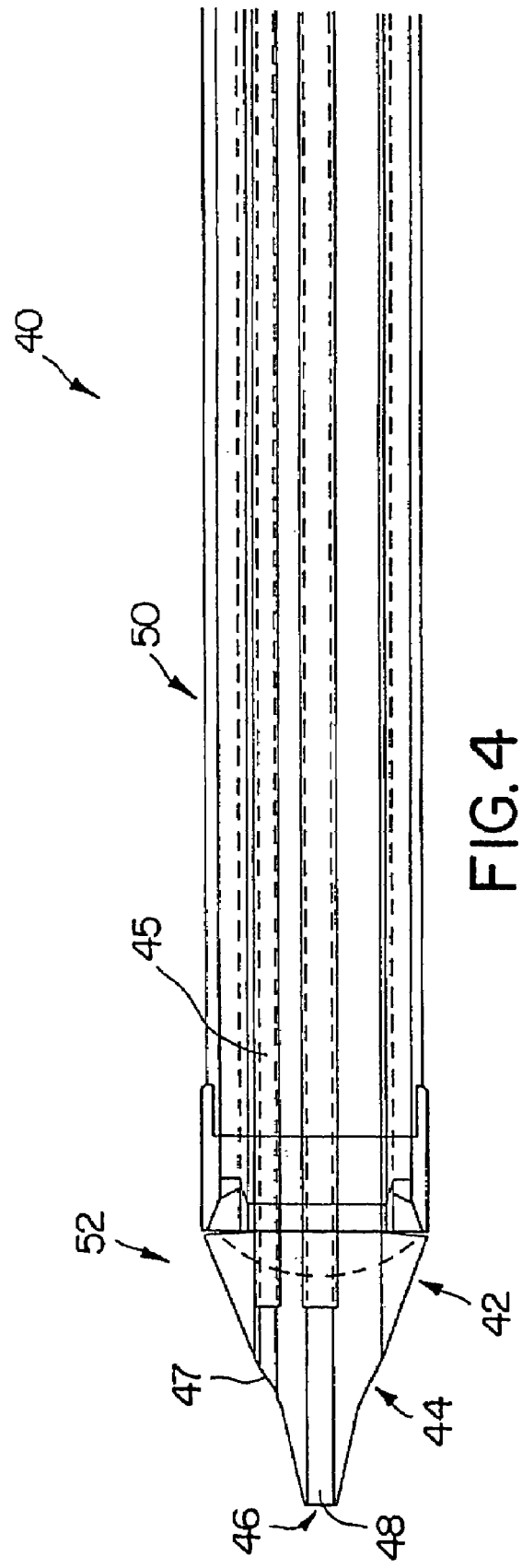

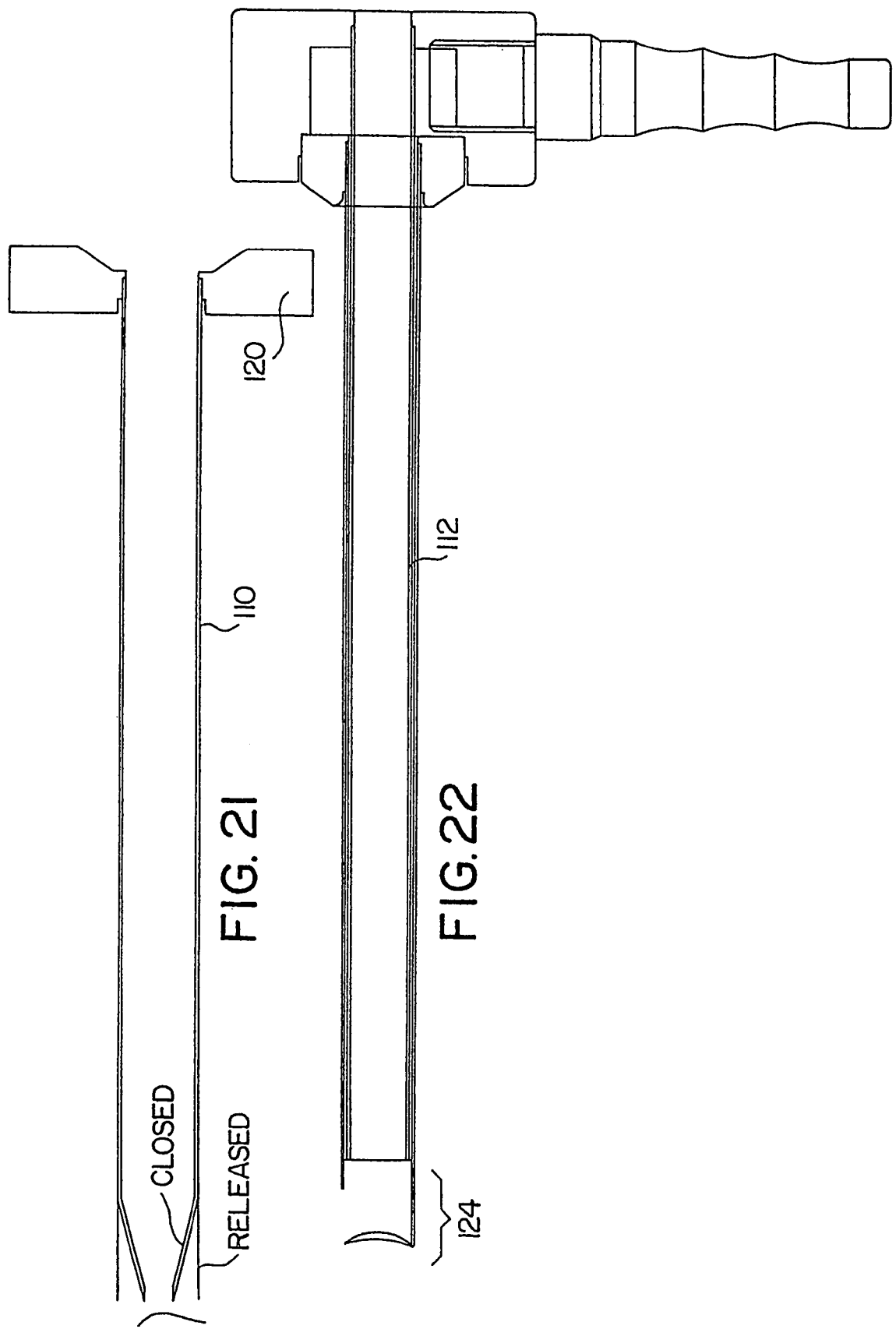

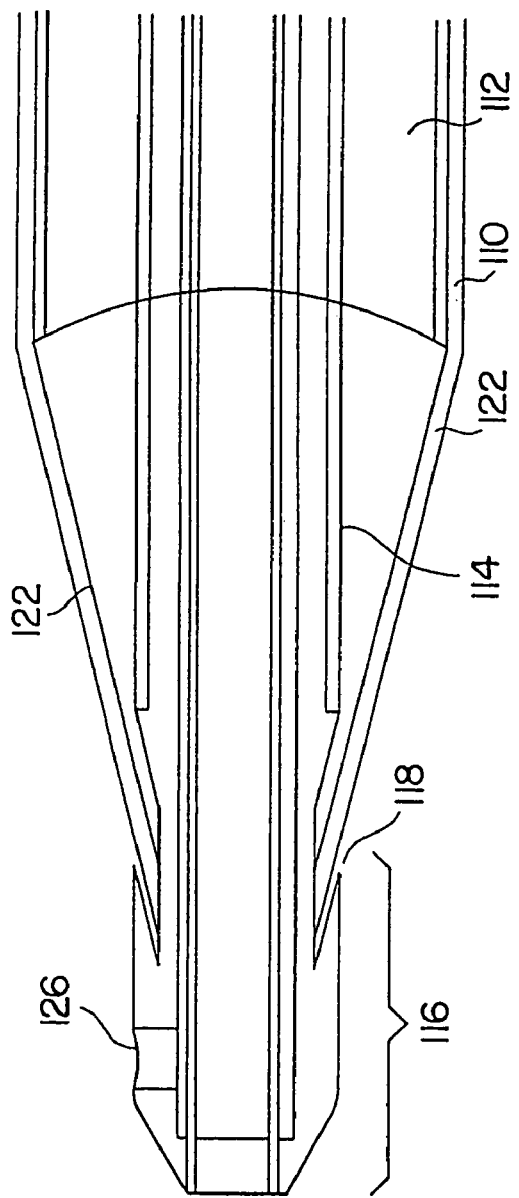
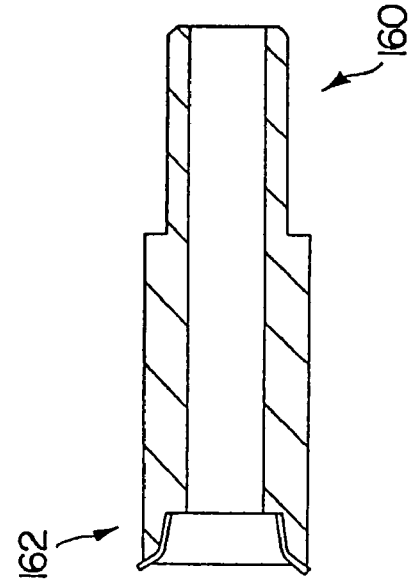
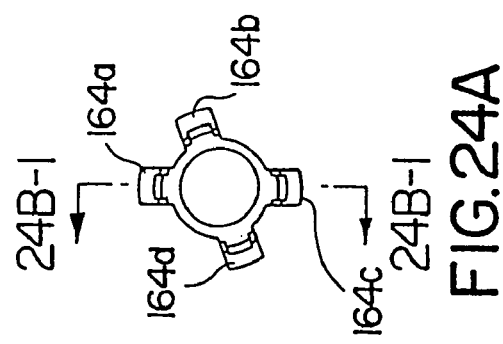

VASCULAR SUCTION CANNULA, DILATOR AND SURGICAL STAPLER

This application is a continuation application under 37 CFR §1.53(b) of application Ser. No. 09/486,185 filed Feb. 18, 2000 now abandoned, which claims priority to U.S. Provisional application No. 60/093,701 filed Jul. 22, 1998, and PCT application No. PCT/US99/16476 filed Jul. 21, 1999, all of which are hereby incorporated by reference in their entirety.

BACKGROUND OF THE INVENTION

1. Field of the Invention

The present invention relates to a vascular suction device, a dilator and a stapler for the closure of a puncture made in the wall of an artery or vein during a medical procedure. The present invention has particular utility for use in and around the femoral artery during and after coronary/cardiac procedures. Other utilities include soft-tissue anchoring, meniscal repair, thoracic lung closure, endoscopic procedures, esophageal repair, laparoscopy, skin/epidermal wound closure and general tissue closure.

2. Description of Related Art

Surgical stapling instruments, dilators and cannulas for diagnostic, interventional and/or therapeutic medical procedures are known. For example, U.S. Pat. No. 5,709,335 issued to Heck discloses a wholly distal surgical stapling instrument for stapling a tubular tissue structure to a luminal structure, such as a vascular lumen. This device can be used for anastomotic stapling of a tubular vessel having two untethered ends, and is especially useful for making the primary anastomotic connection of a bypass vein to a coronary artery or to the aorta. The device essentially includes a rod that is placed within the tubular vessel and an anvil that forces staples (associated with the rod) to bend outwardly against the vessel and a target (such as a coronary artery). Thus, this device requires that the stapler device be placed within the tubular vessel (e.g., vein or artery) for operation. While this device is useful when stapling a graft vein or the like, unfortunately, this device would be inappropriate when the entirety of the tubular tissue is not accessible, such as following percutaneous catheterization procedures.

Another example can be found in U.S. Pat. No. 5,403,333 issued to Kaster et al. This patent discloses a side-to-end anastomotic staple apparatus for use where the end of a blood vessel becomes connected to the side or wall of a second blood vessel or other structure, such as the heart. Similar to the previous discussion, this device requires that at least one end of the vessel be open, so that a stapling mechanism can be inserted therethrough. As noted above, many surgical procedures only access a portion of the vessel. Thus, this device would not be useful in these circumstances.

Yet another example, U.S. Pat. No. 5,695,504 issued to Gifford, III et al., discloses an end-to-side vascular anastomosis device to perform end-to-side anastomosis between a graft vessel and the wall of a target vessel. This device involves a procedure in which the end of a graft vessel is passed through an inner sleeve of the device until the end of the vessel extends from the distal end of the device. The distal end of the graft is then affixed to the wall of the target, using a staple and stapler which forces a staple into both tissues. Similar to the previous disclosures, this device is useful for the attachment of one tubular tissue onto another, however, is inadequate in sealing a puncture in an artery, vein or other tissue left by certain medical procedures.

Other examples can be found in the art. However, these devices are often complicated to manufacture and use, requiring expensive tooling and materials. It is often the case that staplers, cannulas and dilators are single application or procedure devices, which must be discarded after use. Thus, there is a need to provide an efficient stapler mechanism that is simple to use and relatively easy to manufacture, since the device is likely to be discarded after only one use. Moreover, the prior art has failed to provide a device that permits a doctor or clinician to gain access to a puncture site and remain centered on that site throughout the entire procedure, including closure of the puncture, or to ensure that the closure mechanism is delivered over and/or around the puncture site.

SUMMARY OF THE INVENTION

Thus, the present invention solves the aforementioned drawbacks by providing a suction cannula, dilator, stapler and staple that are simple to use and manufacture. In one aspect, the present invention provides a suction cannula that is concentrically aligned with a puncture site (e.g., puncture in an artery or vein) and provides vacuum about the periphery of the puncture site so that the puncture hole is always located during a medical procedure, and to thereby permit a surgeon to quickly and efficiently close the puncture using, for example, a stapling device. In the preferred embodiment the suction cannula has a tube-in-tube construction having an inner tube and an outer tube where a vacuum can be applied between the tubes.

In another aspect, the present invention provides a dilator, which can be placed within the inner tube of the suction cannula during insertion into the body. The dilator (and suction cannula) centers around a guide wire (that is already in place within the venous structure) and follows the path of the guide wire to the puncture site. Preferably, the dilator has a tapered tip on the distal end that follows the guide wire though the puncture hole made in the vein or artery. A blood indicator is provided on the proximal end to provide visual feedback when the surgeon is in the artery (i.e., pulsating blood indicates that the tip of the dilator is in the artery). In one preferred embodiment, the dilator includes a tapered tip on the distal end that is radially collapsible so that the dilator can be withdrawn from the artery and the suction cannula is thereby permitted to advance over the dilator to the artery wall. To that end, indicators on the external, proximal end of the dilator provide the user with a visual measurement as to the distance to the artery wall. Once the suction cannula makes contact with the vascular wall, and vacuum can be applied to the cannula so that the cannula remains concentrically aligned with the puncture in the vessel, and the dilator can be removed.

In yet another aspect of the present invention, a stapler is provided which holds a multi-pronged staple on a shaft at the distal end. The distal portion of the stapler is constructed to fit within the suction cannula (i.e., the inner tube of the cannula) to approach the puncture in the wall of the artery (or other soft tissue), to permit the stapling of the artery. Preferably, the distal end of the stapler includes a T-flange that retains a staple, and a deploying mechanism that deploys the staple into the artery, thereby sealing the puncture. Deployment of the staple can include crimping of the staple through the vascular wall and/or partial insertion of the staple into the tissue. The T-flange permits the staple to be retained on the distal end of the stapler and deployed into the artery wall. An oval hub on the T-flange is provided that mates with an oval hole in the center of the staple. To hold a staple, a staple is placed on the hub and rotated 90 degrees, thereby affixing the staple to the stapler. Once the staple is crimped onto the artery wall, the shaft can be rotated 90 degrees, thereby aligning the oval hub and the oval hole, so that the stapler can be removed. Preferably, the staple includes a plurality of prongs that are inserted into the vascular wall.

Advantageously, the suction cannula of the present invention permits the surgeon to remain centrally located about a puncture site throughout the entire procedure, from incision to closing. The suction cannula permits a surgeon to enter an incision, and using a dilator as an artery indicator, secure the cannula to the artery wall, via vacuum force, about the puncture site. Also advantageously, this permits the surgeon to view and approach the puncture site (using a catheter, for example) throughout the entire procedure, without obstruction. In addition, a stapler and staple are provided which can be guided down the shaft of the cannula to quickly seal the puncture site.

It will be appreciated by those skilled in the art that although the following Detailed Description will proceed with reference being made to preferred embodiments, the present invention is not intended to be limited to these preferred embodiments. Other features and advantages of the present invention will become apparent as the following Detailed Description proceeds, and upon reference to the Drawings, wherein like numerals depict like parts, and wherein:

BRIEF DESCRIPTION OF THE DRAWINGS

FIG. 4 is a detailed view of the distal end of one embodiment of the dilator of the present invention;

FIG. 21 depicts the outer sheath of the cannula embodiment of FIG. 20;

FIG. 22 shows the cannula of the embodiment of FIG. 20;

FIG. 23 depicts a detailed view of the tip section of the dilator of FIG. 20;

FIGS. 24A and 24B depict a cross sectional view and a side view, respectively, of an alternative tip portion of the stapler of the present invention;

DETAILED DESCRIPTION OF THE INVENTION

Figure 1:
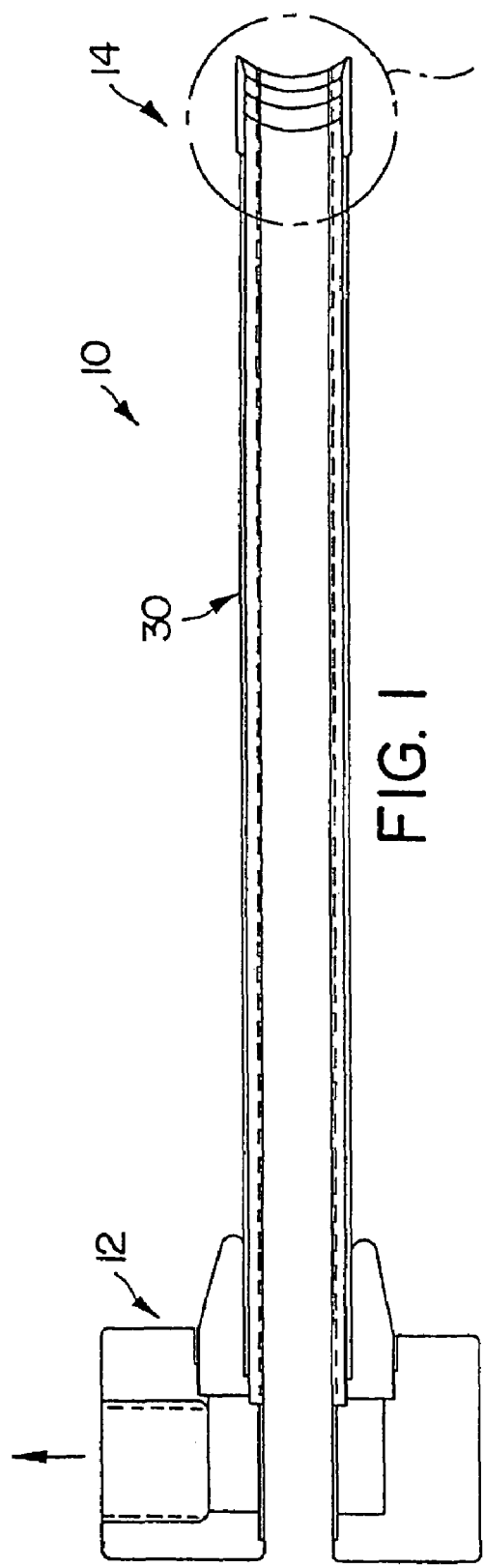
FIG. 1 is a longitudinal cross-sectional view of one embodiment of the suction cannula of the present invention.
Figure 3B:
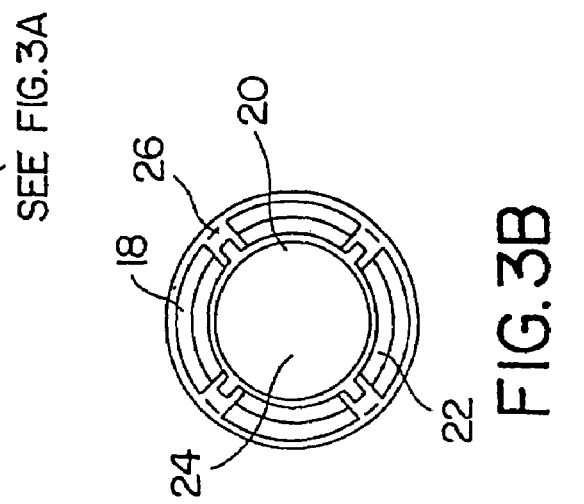
FIG. 3B is an end-on cross sectional view of the distal end of the suction cannula of FIG. 3A.
Figure 3A:
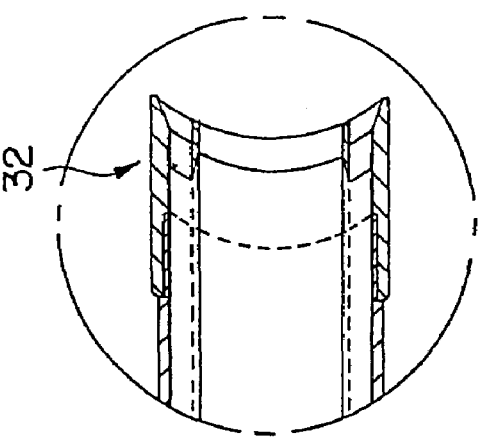
FIG. 3A is an enlarged cross-sectional view of the distal end of the suction cannula of FIG. 1.
Figure 2:
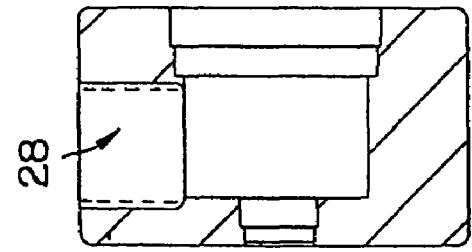
FIG. 2 is a cross-sectional view of the hub portion of the suction cannula of FIG. 1.

FIGS. 1–3B depict various views of one embodiment of the suction cannula 10 of the present invention. Essentially, cannula 10 comprises a tubular member 30, a proximal end 12 and a distal end 14. The distal end 14 is adapted to permit vacuum affixation of the cannula 10 to a vascular wall, or other tissue as will be described below. As shown in FIG. 3B, the tubular member 30 is preferably constructed with a tube 20 within a tube 18. As will be described below, the chamber 22 between the tubes 18 and 20 is used as a vacuum chamber. Passage 24 permits a dilator and/or stapler device (each discussed below) and/or other surgical devices to pass therethrough. Support members 26 are provided to concentrically affix tubes 18 and 20. The proximal end 12, as shown in FIG. 2 includes a vacuum port 28 that can be attached to an external vacuum (not shown). Vacuum port 28 communicates with chamber 22 (between inner tube 20 and outer tube 18) to provide a vacuum therein. As shown in FIG. 3A, a flexible tip section is provided on the distal and 14 of the cannula to provide a secure vacuum interface between cannula 10 and a vascular wall. Preferably, the flexible tip section is formed of pliable rubber or other equivalent materials.

Figure 8:
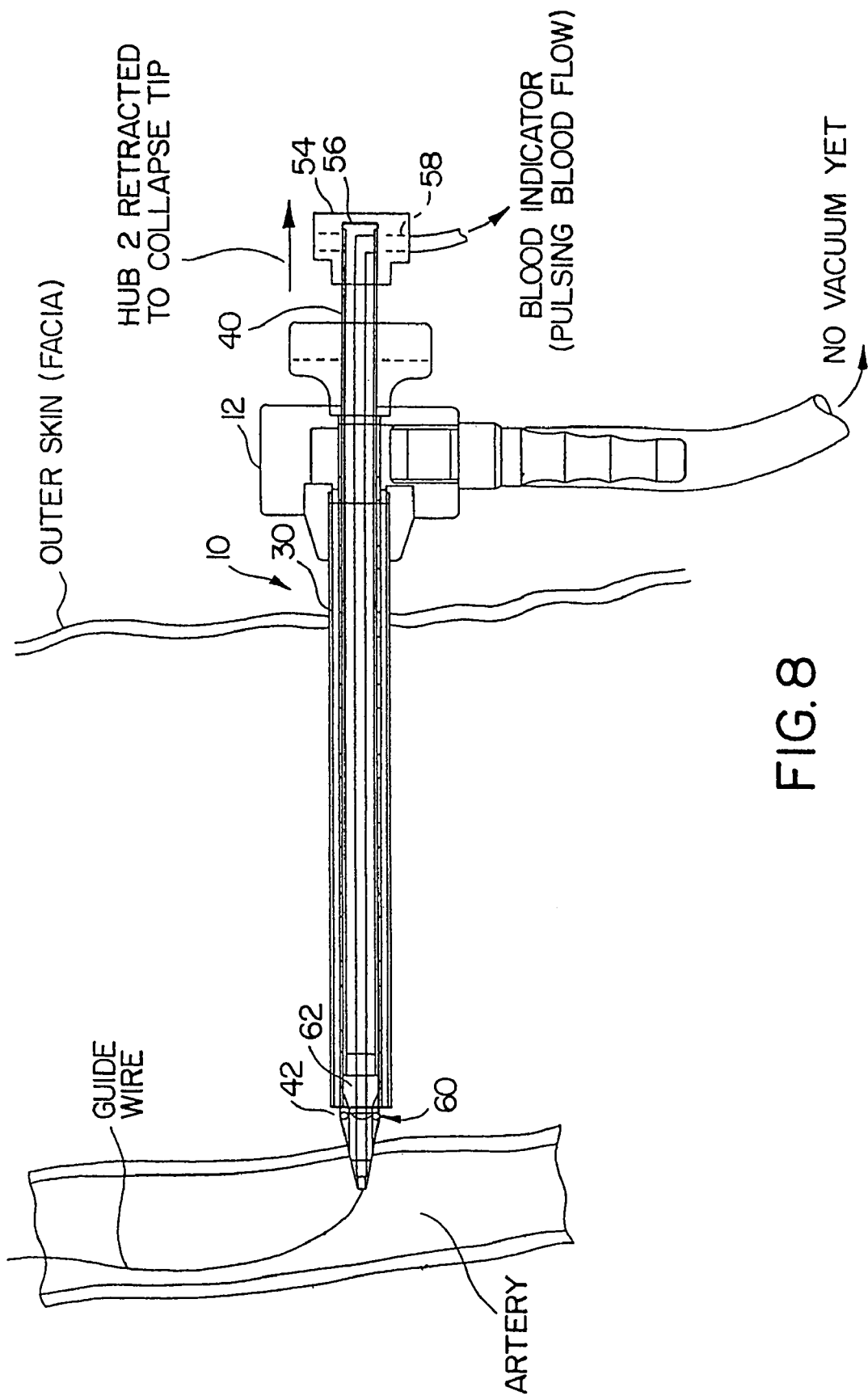

FIG. 4 depicts one preferred embodiment of a dilator 40, used in conjunction with the suction cannula 10, described above. The dilator includes a tubular structure 50, a distal end 52 and a proximal end 54 (not shown in FIG. 4). The tubular structure 50 is intended to pass within the inner tube 20 of the suction cannula 10. Thus, the diameter of tubular structure 50 is preferably manufactured to the tolerance of the inner tube 20, to permit unobstructed ingress and egress of the dilator 40 within the cannula 10. The distal end 52 preferably includes a dilator tip 44, a passage 46 for a guide wire 48, and a collapsible section 42 that can be hand-manipulated to expand and contract (described below). Additionally, another tube 45 is provided within tube 50 in fluid communication with opening 47 and hub (described below) to allow blood to flow within tube 45. Tube 45 can be eccentrically disposed within tube 50 (as shown), or, tube 45 can be concentrically disposed within tube 50. Referring to FIG. 8, the proximal end 54 of the dilator includes a movable hub 56. A cam mechanism 62 connected between movable hub 56 and collapsible section 42 (via one or more connecting members, not shown) that engages an O-ring 60 to collapse and/or expand section 42. Preferably, when section 42 is expanded, the diameter of section 42 is larger than the diameter of tube 20, thereby locking the dilator 40 against the cannula tube 30 (described herein). When it is desired to remove the dilator from the cannula, section 42 is collapsed so that the dilator can pass within tube 20 of the cannula 30.

Figure 4A:
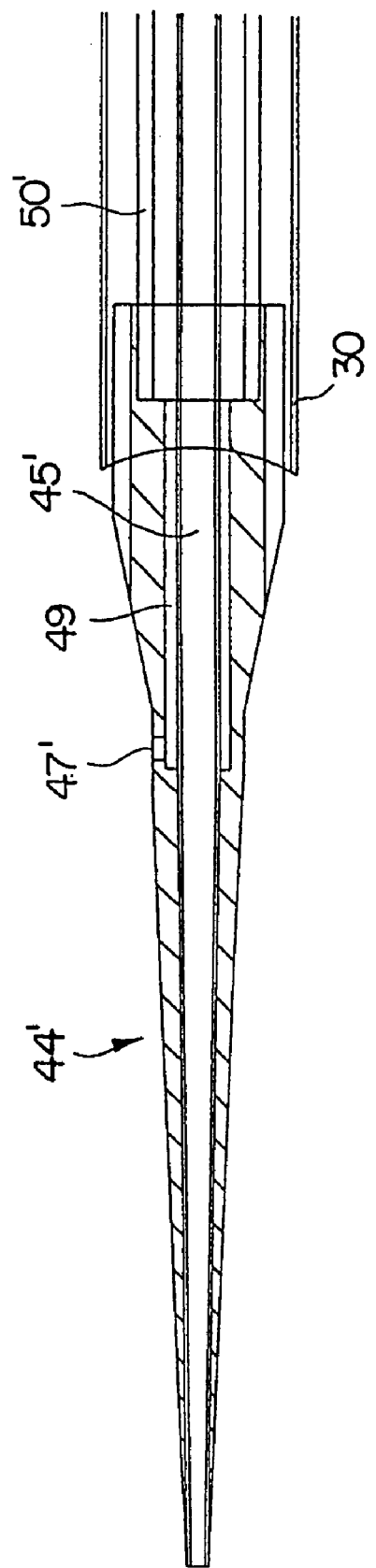
FIG. 4A is a detailed view of an alternative embodiment of the tip section of the dilator of FIG. 4.

FIG. 4A depicts an alternative embodiment for the tip section 44' of the dilator depicted in FIG. 4. In this embodiment, tip section 44' has an elongated shape, as compared with the embodiment in FIG. 4. Like the previous embodiment, opening 47' permits fluid to flow within region 49, which is disposed within tube 50' around tube 45'. Unlike the previous embodiment, tube 50' and tip 44' are not fixed within the cannula 30. Rather, tube 50' and tip 44' can be inserted into and withdrawn from the cannula with relatively little obstruction.

Figure 5:
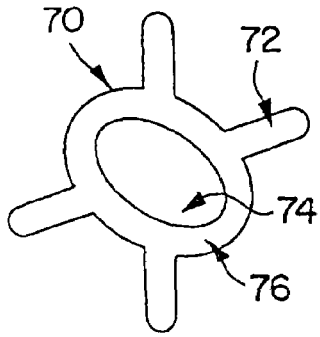
FIG. 5 is a perspective view of the preferred staple of the present invention.
Figure 6A:
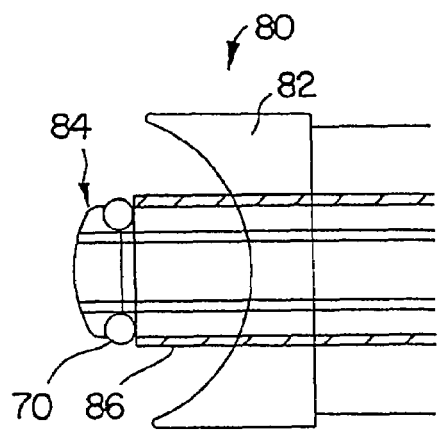
FIG. 6A is a view of the distal end of one embodiment of the stapler of the present invention.
Figure 11:
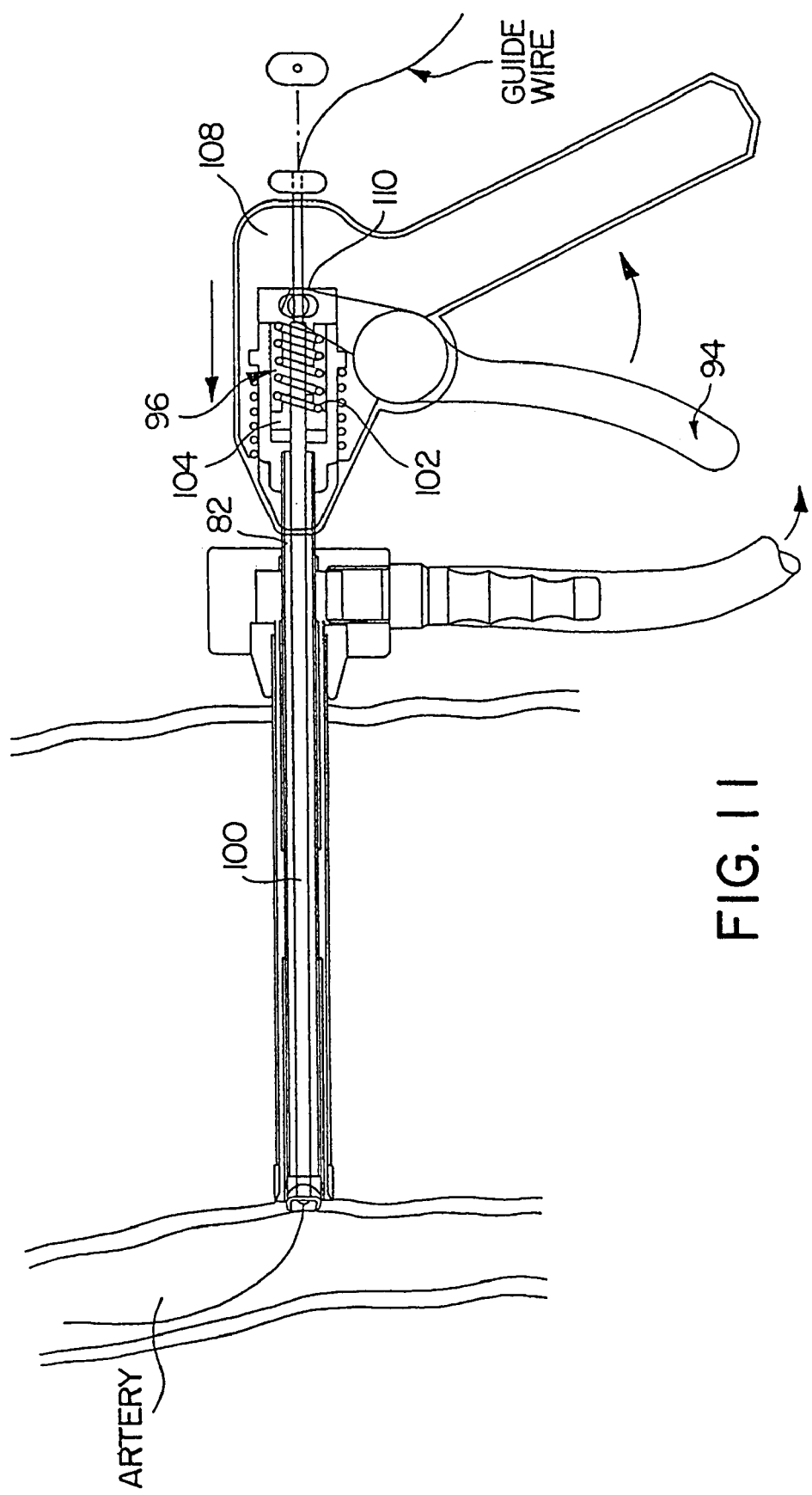
Figure 12:
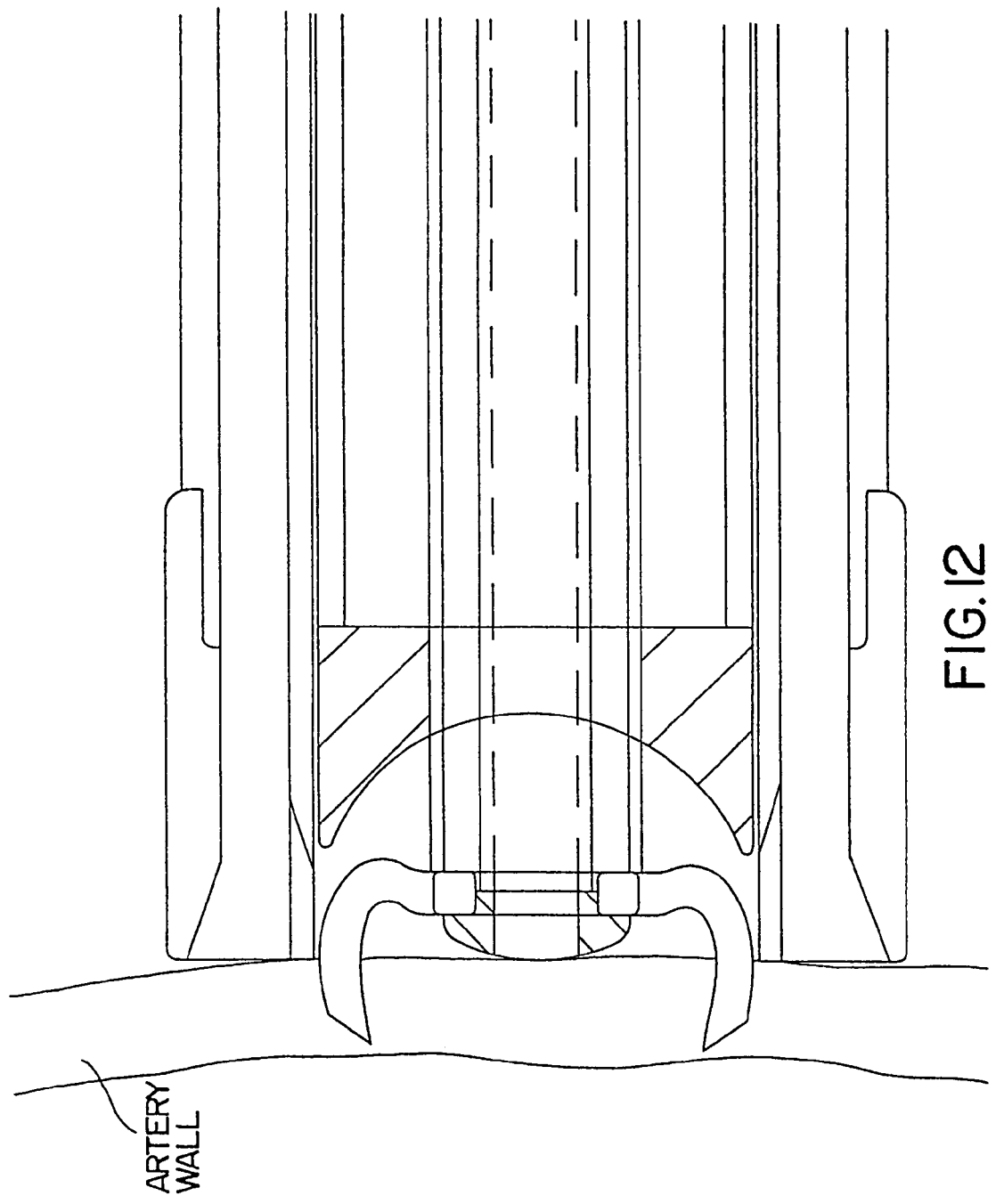
Figure 15:
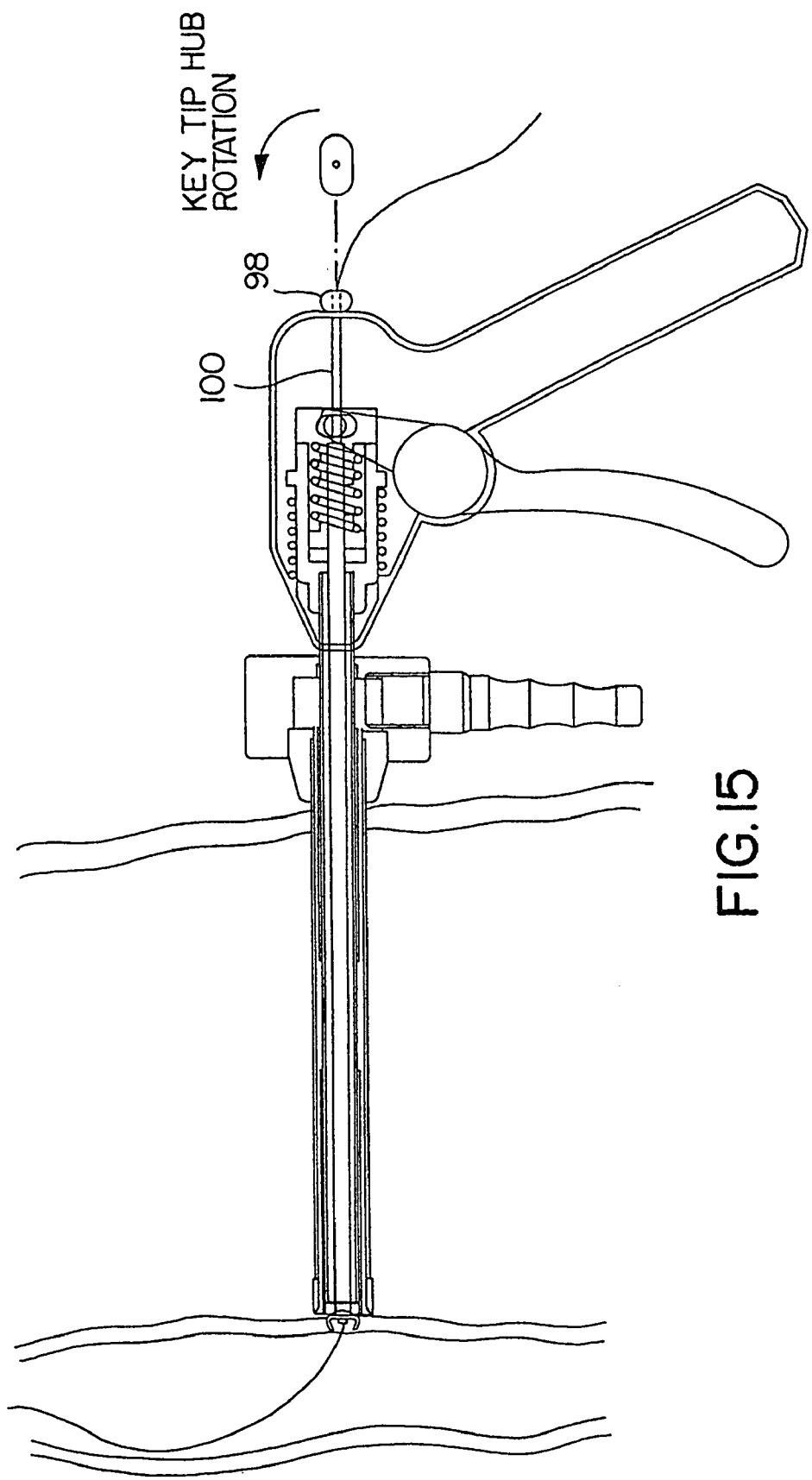

FIG. 5 depicts the preferred embodiment of the surgical staple 70 of the present invention. Staple 70 includes an oval member 76 with a plurality of prongs 72 around the circumference of oval member 76. Oval member 76 defines an oval opening or hole 74, which cooperates with a stapler (described below). As will be described in more detail with reference to the stapler device, prongs 72 crimp onto the vascular walls (or other tissue) to effectively seal a puncture. FIG. 6A shows a view of the distal end of the stapler 80 of the preferred embodiment. The distal end includes a slidable crimping member 82 and a flange member 84. As shown in FIG. 6E, flange member 84 is shaped to match the inner diameter of oval member 76 of the staple 70. In use, staple 70 is inserted over flange member 84 so that staple 70 abuts shaft member 86 adjacent flange member 84. Staple 70 is rotated approximately 90 degrees, as depicted in FIG. 6D, thereby locking the staple between flange 84 and shaft 86. Flange member 84 is connected to connecting rod 100 (as shown in FIGS. 11 and 15) passing through the stapler device to the proximal end. Accordingly, key hub 98, which is also connected to connecting rod 100 (and thus, flange member 84) can be rotated approximately 90 degrees, thereby releasing the staple 70 from the staple device. In the preferred embodiment, key hub is hand rotatable. Although, key hub, connecting rod and flange member can also be automatically rotated through the action of the driving mechanism and handle, 96 and 94.

Figure 6B:
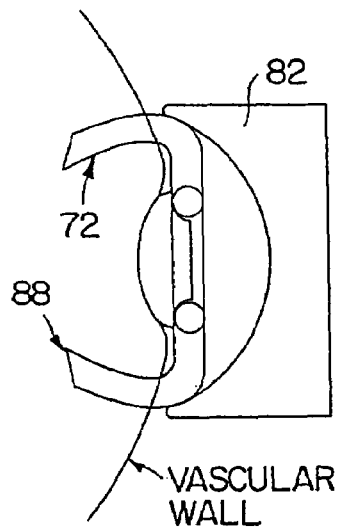
FIG. 6B is a detailed view of the stapler of FIG. 6A in cooperation with the preferred staple of the present invention.
Figure 6C:
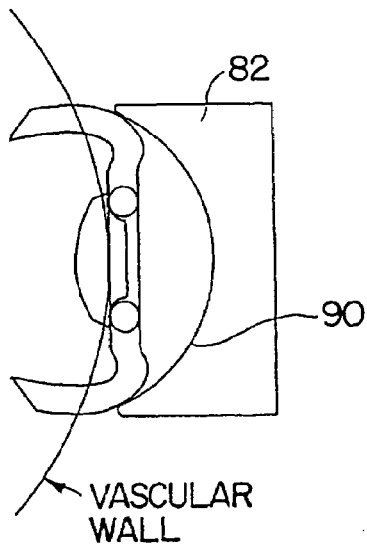
FIG. 6C is another detailed view of the stapler of FIG. 6A in cooperation with the preferred staple of the present invention.
Figure 6D:
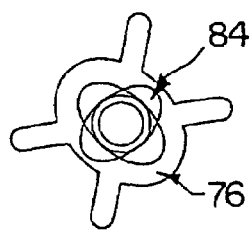
FIG. 6D is another detailed view of the stapler of FIG. 6A in cooperation with the preferred staple of the present invention.
Figure 6E:
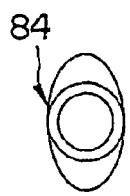
FIG. 6E is an end-on view of the flange portion of the distal end of FIG. 6A.

FIGS. 6B and 6C depict insertion of the staple into the vascular wall (or other tissue) and crimping of the staple, respectively, using the stapler 80, described above. Crimping member 82 is first slid toward the vascular wall so that the staple 72 pierces the wall (FIG. 6B). It will be understood that the members 72 can include a sharp or pointed edge 88 to aid the insertion of staple 70 into the vascular wall. Crimping member 82 is then further advanced toward the vascular wall to force the staple to crimp, due to the force direction exerted by the conforming portion 90 onto the staple (FIG. 6C). In this embodiment, conforming portion 90 includes a generally parabolic shape. Once the staple is crimped, the flange member 84 can be rotated (e.g., rotated 90 degrees, via connecting rod 100 and key hub 98) so that hole 74 and flange 84 are aligned, and the stapler can be withdrawn from the vascular wall.

Figure 6F:
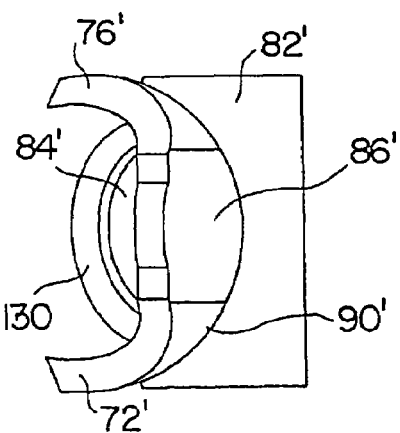
FIG. 6F is a side view of another preferred staple of the present invention in cooperation with the crimping member.

Referring to FIG. 6F, another embodiment of a staple 76' of the present invention. The staple of this embodiment cooperates with the flange member 84', crimping member 82', conforming portion 90' and shaft 86' as in the previous embodiment. Included in this embodiment is membrane 130. Membrane 130 is formed on the staple between members 72' such that the opening 74 (not shown) is covered. The membrane 130 is preferably formed to permit unobstructed ingress and egress of flange 84' within the opening 74, as shown in the drawing. Membrane 130 is formed of silicone, elastomer, or bioabsorbable material. Essentially, membrane 130 is provided to seal the puncture hole in the vascular wall that may remain unsealed due to the opening 74 of the staple 76'.

Figure 7:
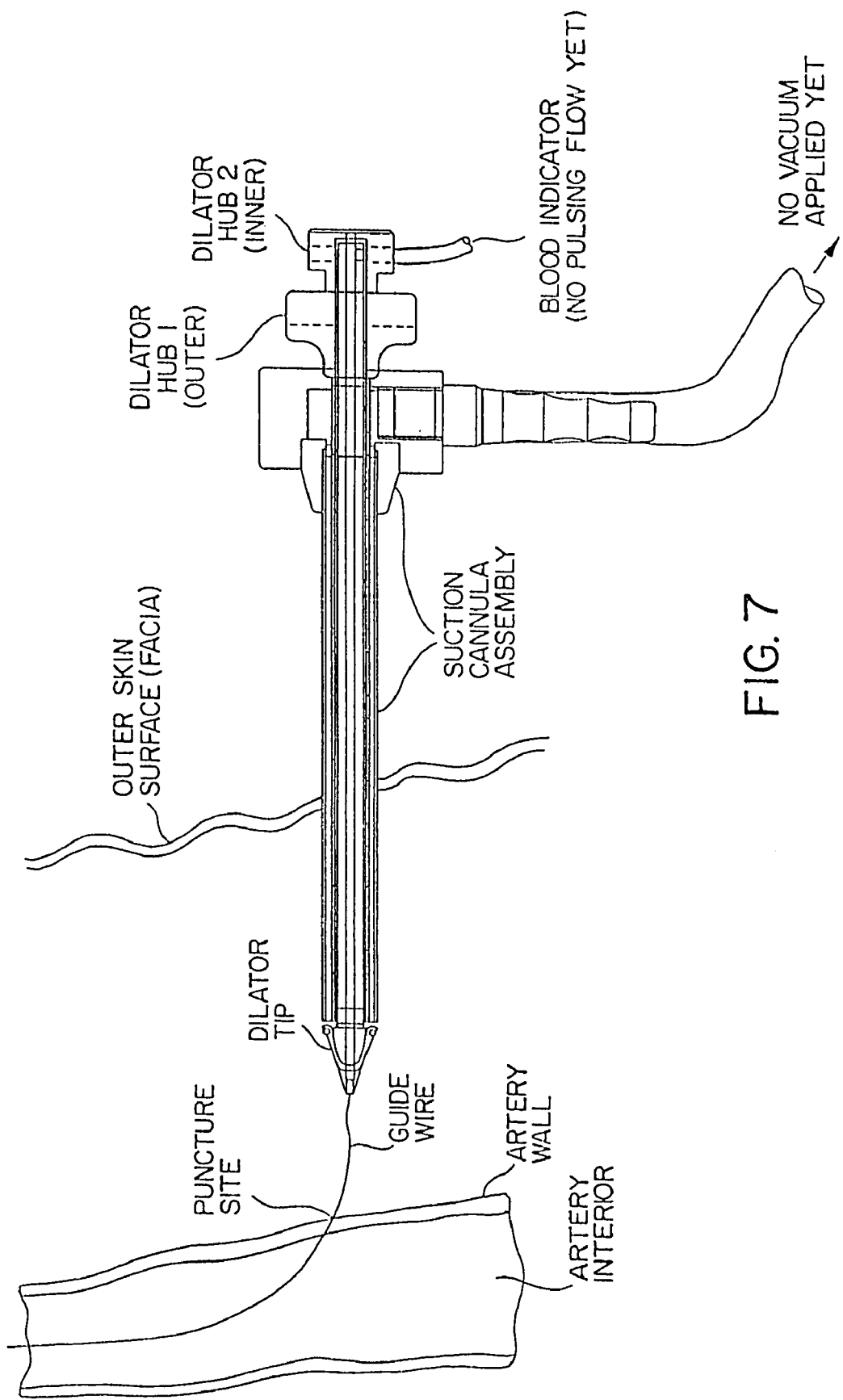
FIGS. 7–19 show the operation of a preferred sequence of the present invention
Figure 9:
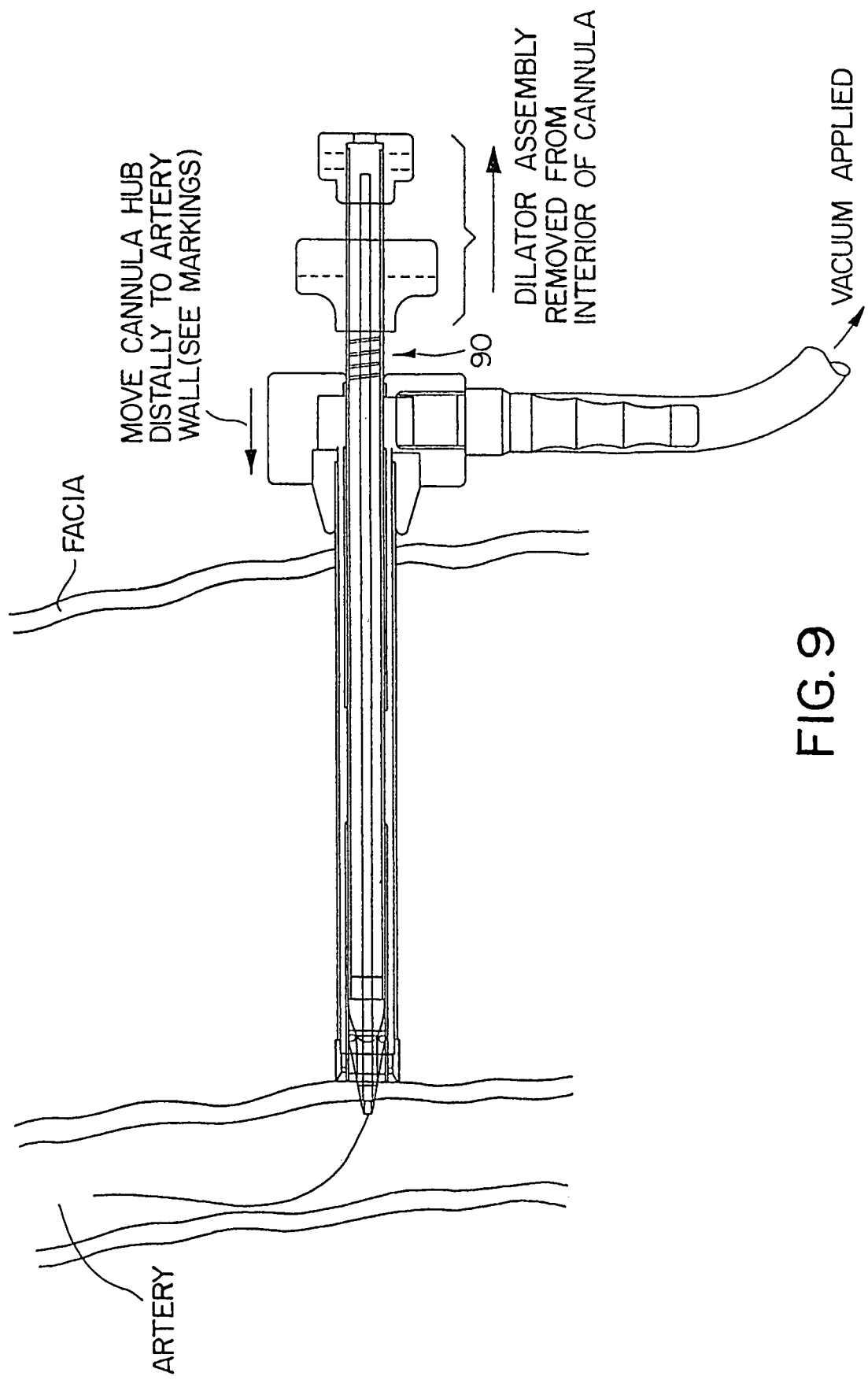
Figure 10:
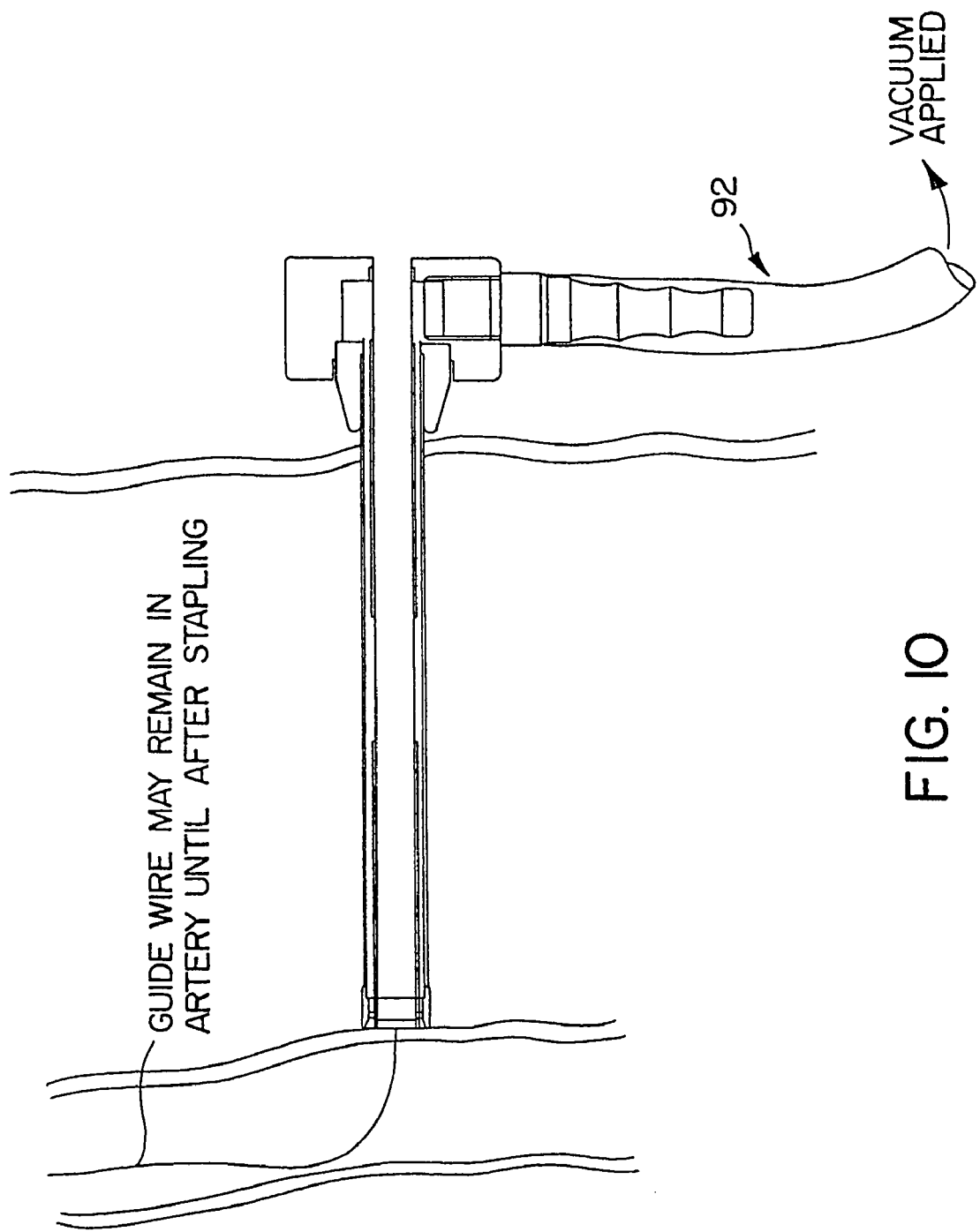

FIGS. 7–19 depict detailed functionality of the cannula 10, dilator 40, staple 70 and stapler 80 (as described above with reference to FIGS. 1–6E) of the present invention. As shown in FIG. 7, the suction cannula 10 and the dilator 40 are inserted into the incision in the skin (facia), following the previously-inserted guide wire 48, toward the arterial puncture site. Although not shown in these drawings, the guide wire can be removed at any stage of the proceeding process, or may be left within the cannula as a reference point. It should be noted that with reference to the stapling procedure described herein, it is preferable that the guide wire be removed. When the tip 44 of the dilator 40 enters the puncture site, pulsating blood at the proximal end 54 of the dilator provides visual feedback, as shown in FIG. 8. Importantly, the dilator provides concentric alignment with the puncture site about the guide wire. Once inside the artery, the tip is collapsed (as described above) by pulling back on the proximal hub 56 of the dilator, while simultaneously the cannula 10 is advanced over the dilator tip (distally) to engage the artery wall, as shown in FIG. 9. Graduated markings 90 on the dilator provide an indication of the relative distance to the artery wall. As shown in FIG. 10, the dilator is removed and vacuum source 92 is applied to the cannula to secure the cannula to the artery wall. Advantageously, using the cannula as described herein, unobstructed access to a puncture site is obtained, permitting a surgeon' to perform intravascular procedures without the need for various "changeouts" of instruments to locate the puncture site.

Figure 13:
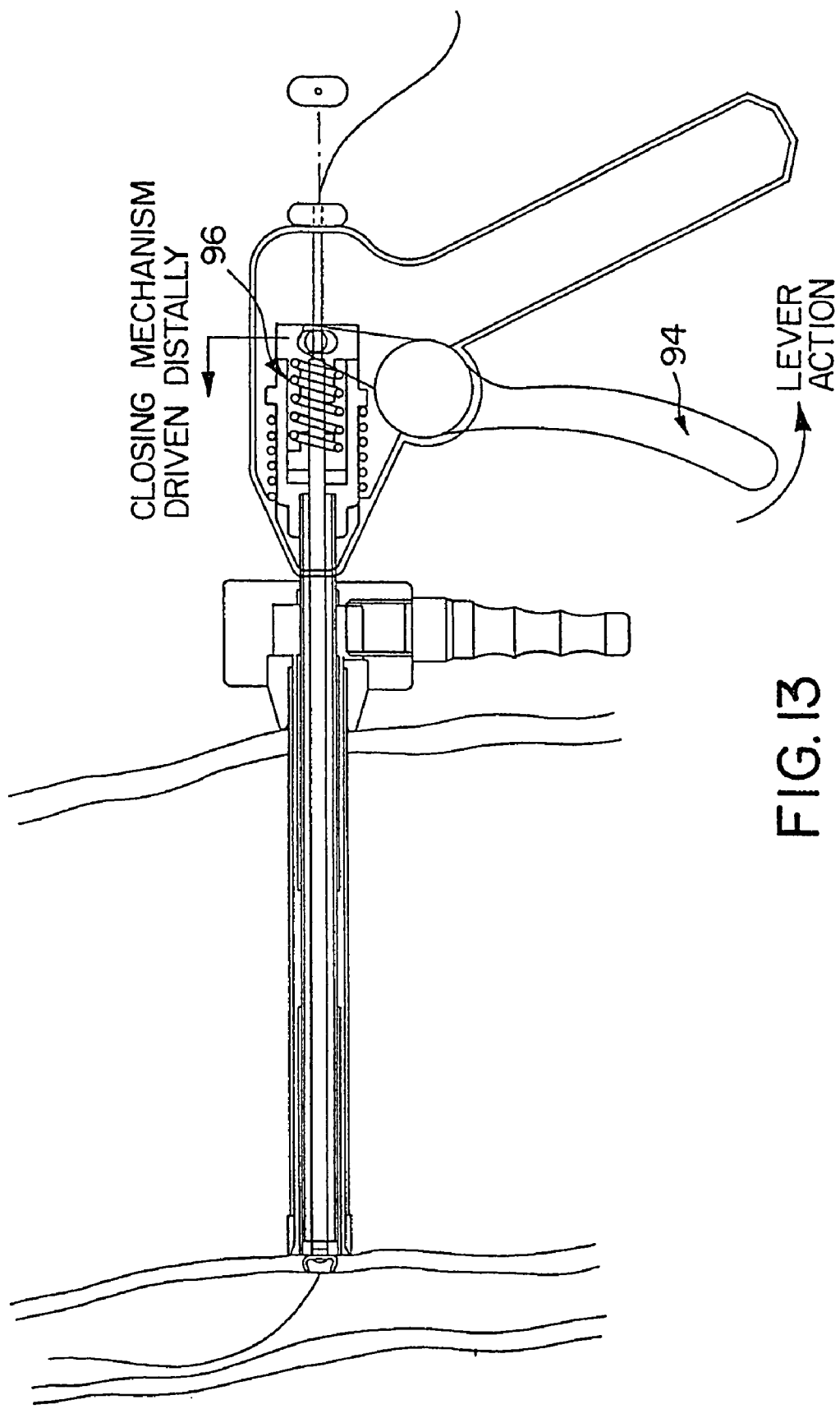
Figure 14:
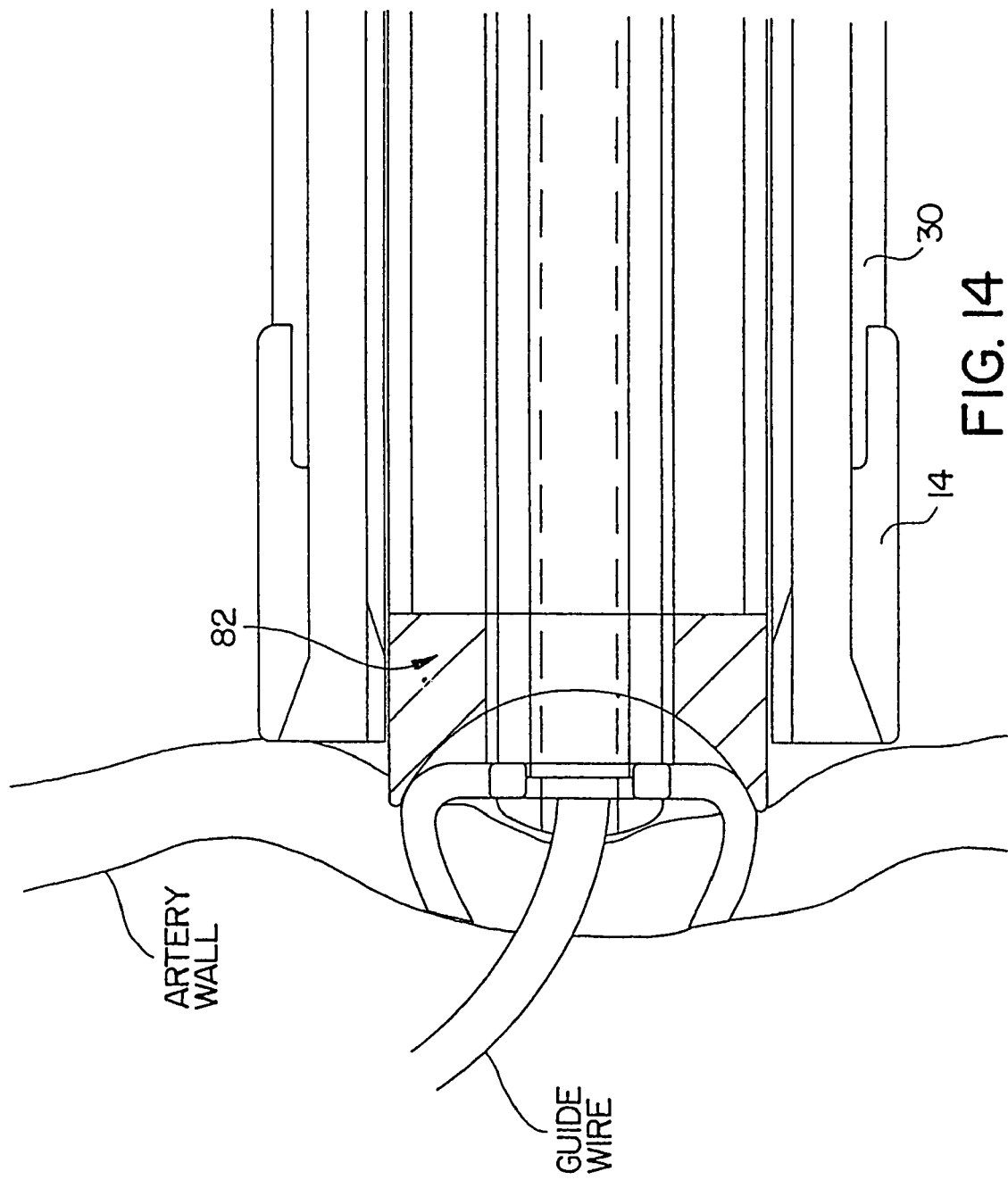
Figure 16:
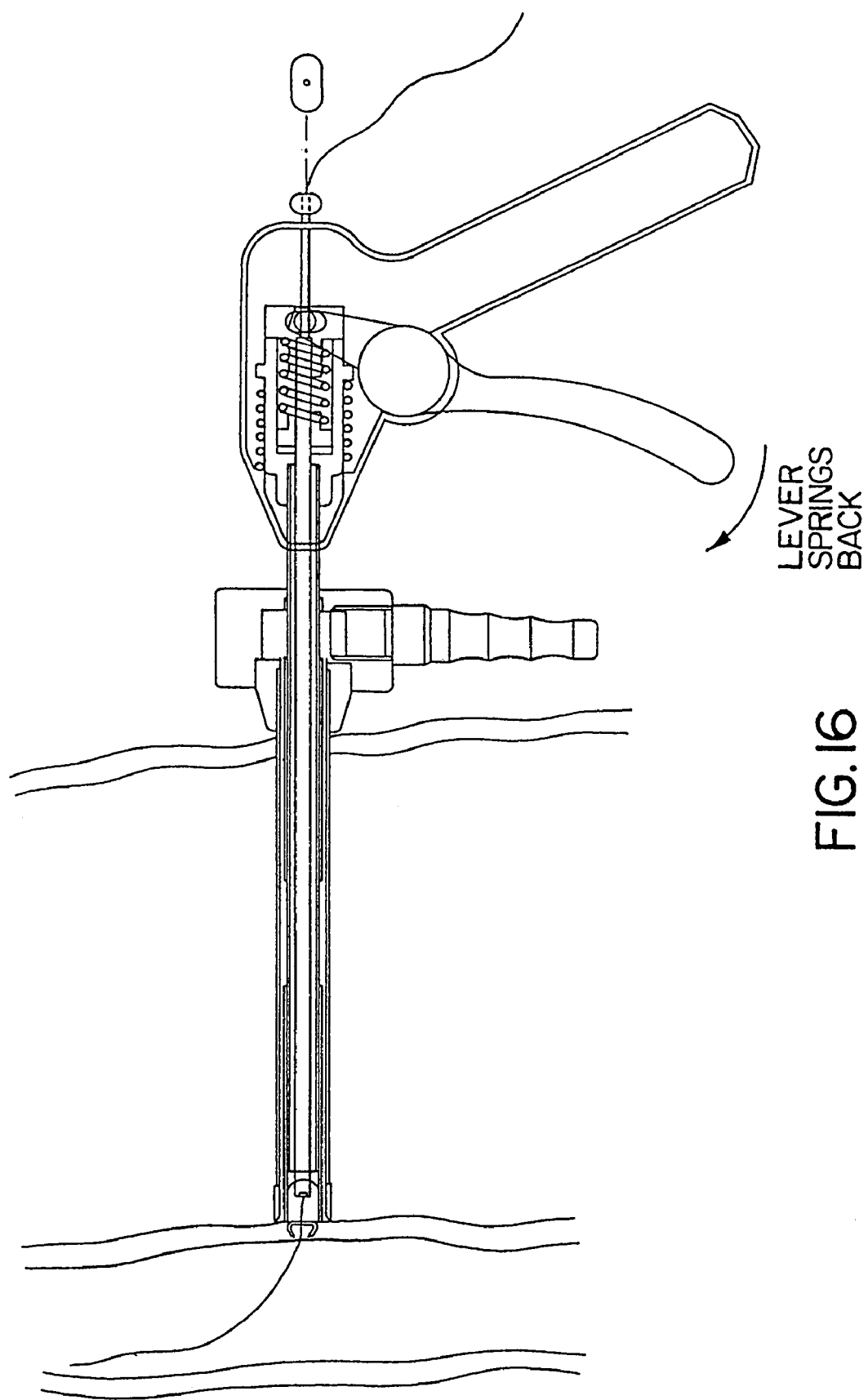
Figure 17:
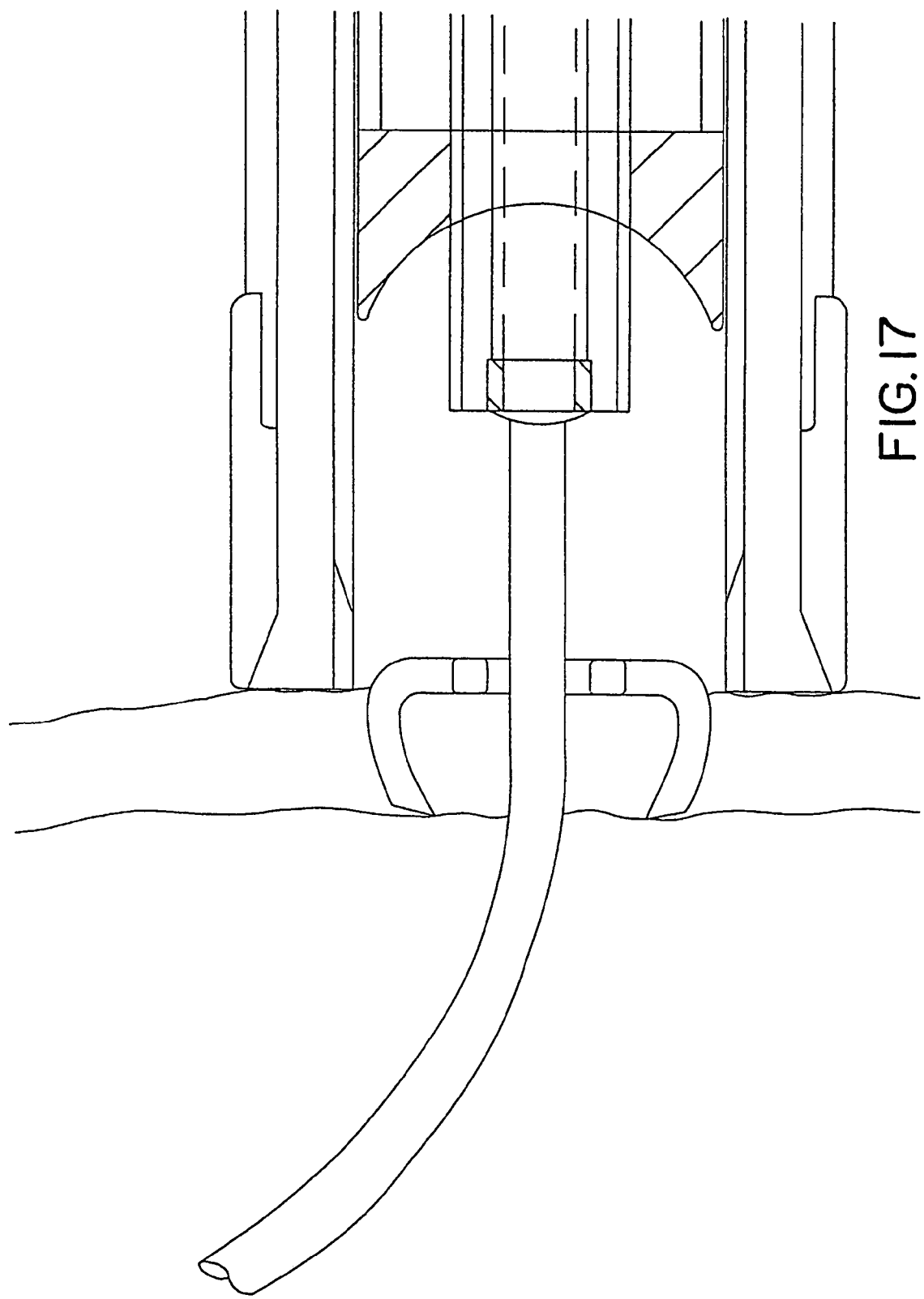
Figure 18:
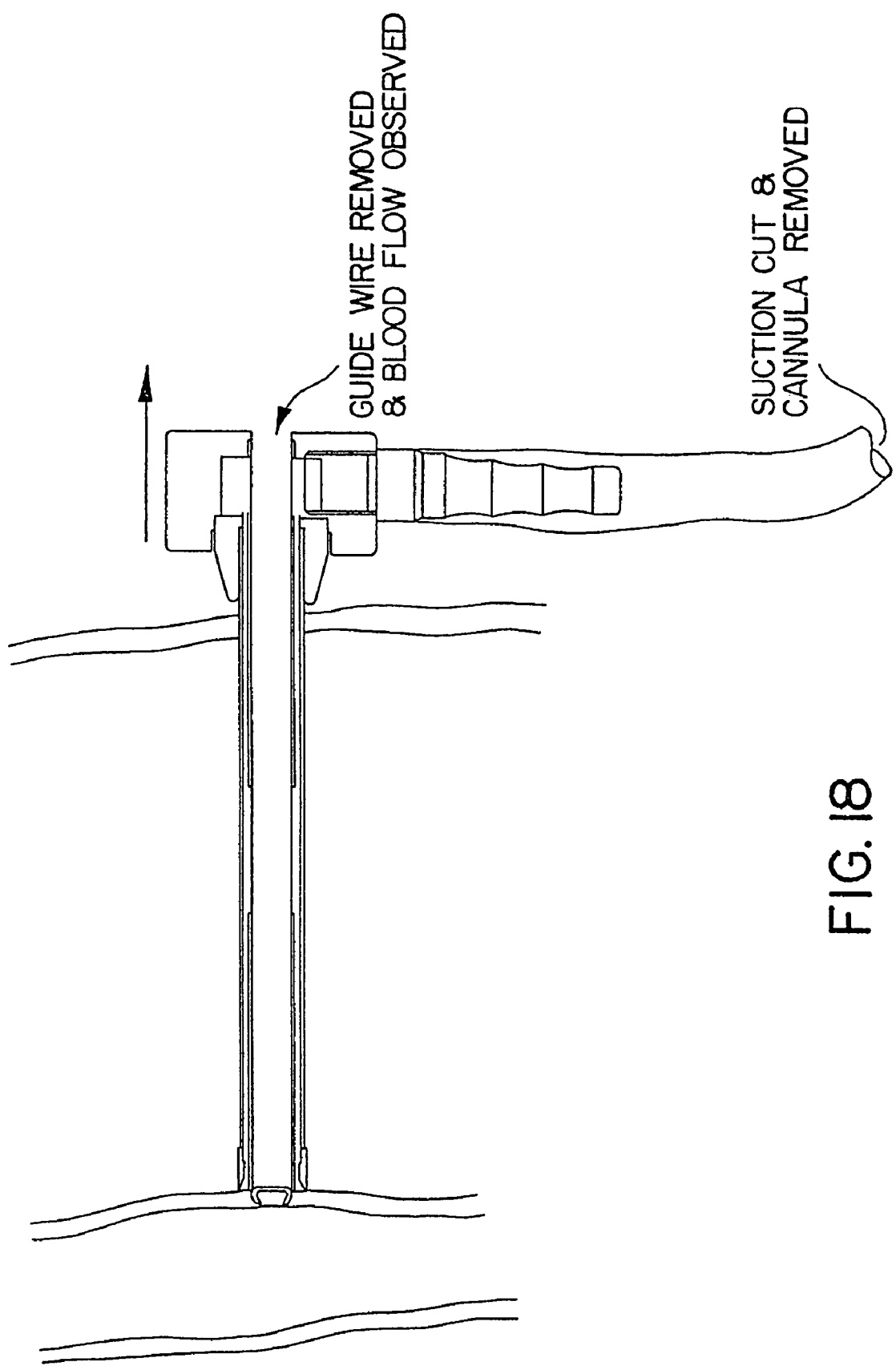
Figure 19:
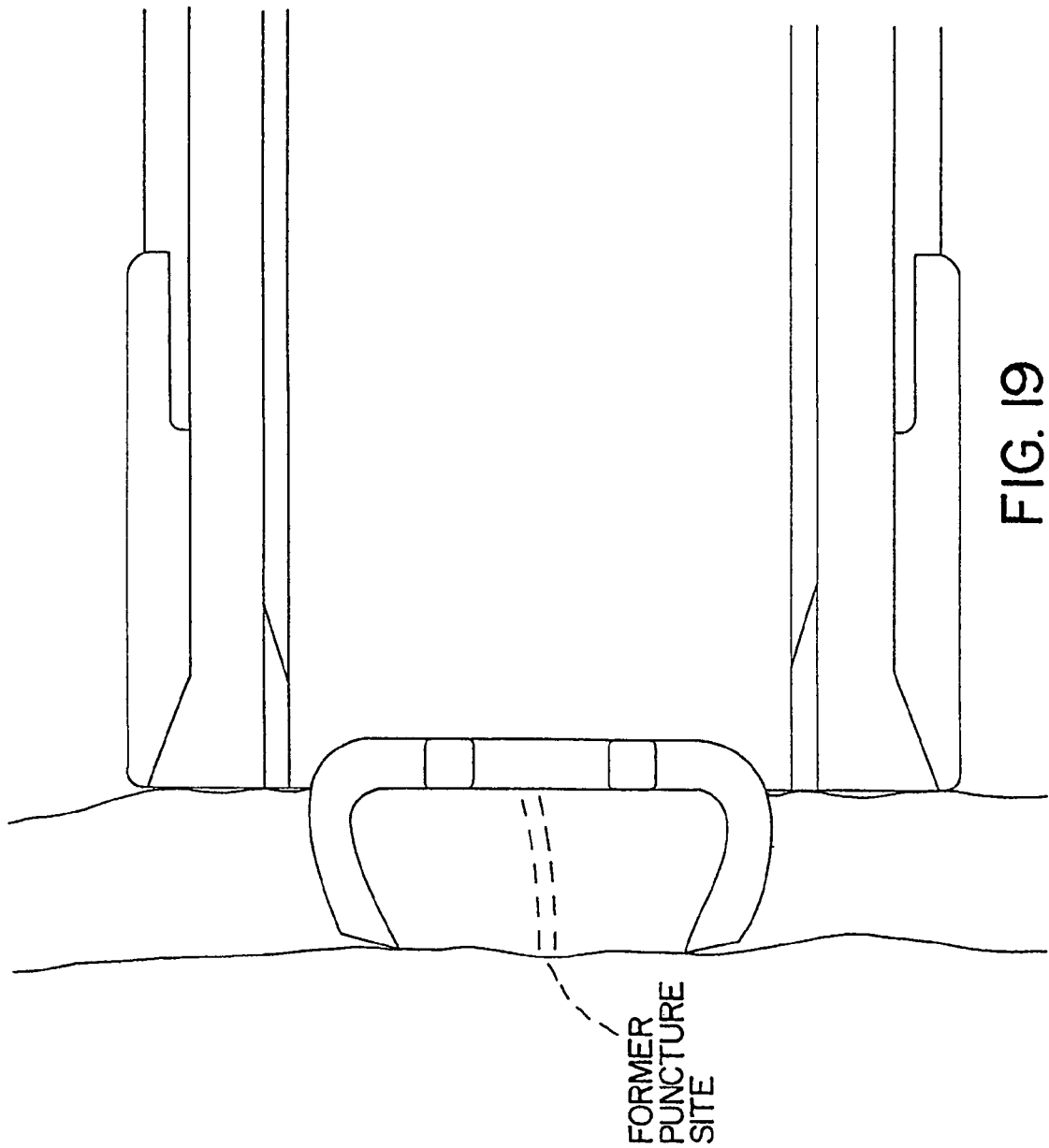
Figure 20:
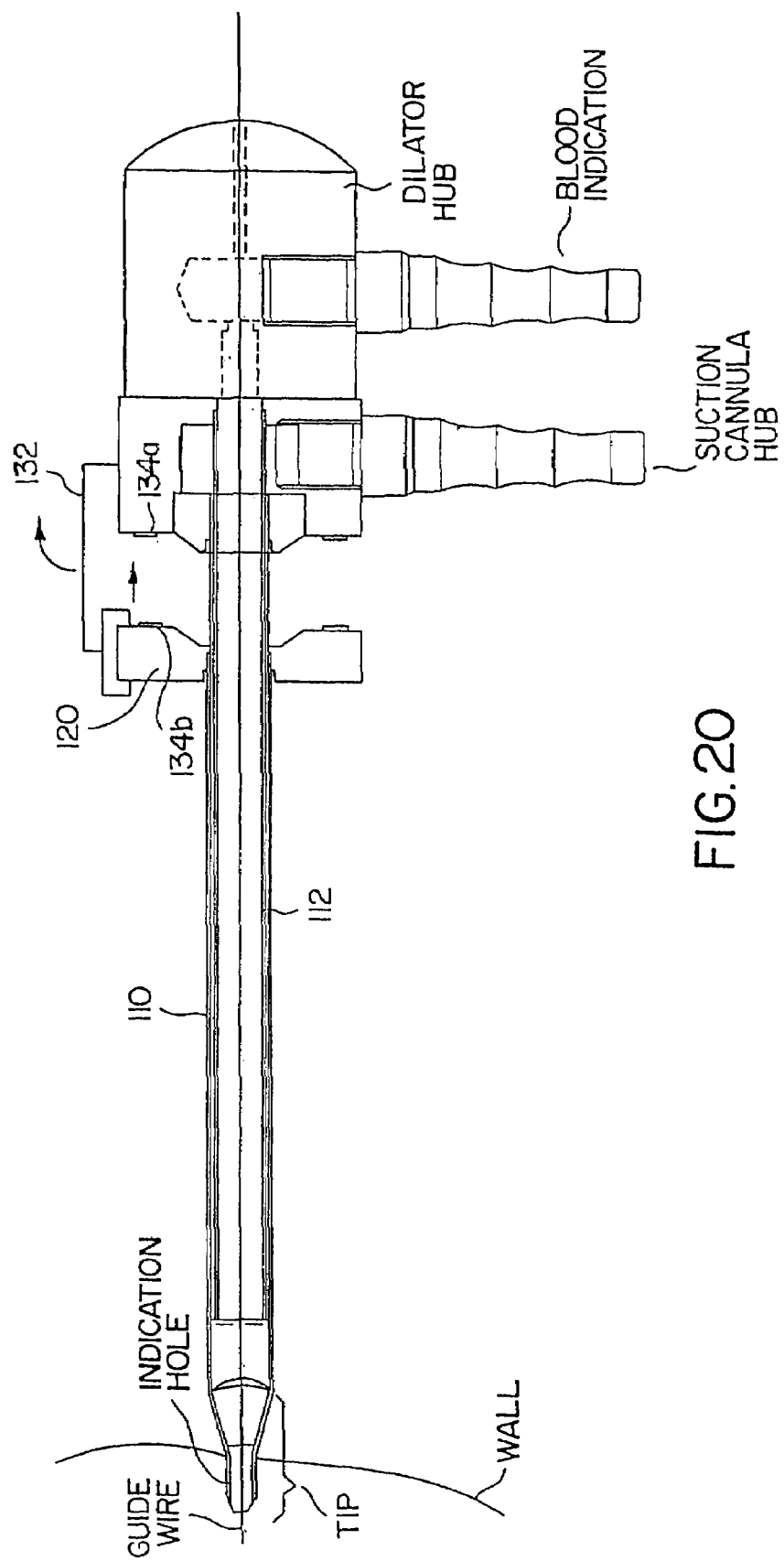
FIG. 20 depicts another embodiment of the cannula and dilator of the present invention.

Once the diagnostic, interventional, therapeutic, or other procedure (following the cannula to the puncture site) is complete, the puncture site is to be closed. As shown in FIG. 11, the stapler 80 (with a staple 70 secured on the distal end, as described above) is inserted down the cannula to the puncture site. The staple 70 is pushed into the vascular wall sufficiently to allow the staple to at least partially pierce the wall, as shown in the close-up view of FIG. 12. As shown in FIGS. 13 and 14, the surgeon activates a lever 94, which, in turn activates driving mechanism 96 to drive crimping member 82 distally, to thereby crimp the staple and seal the puncture site (as described above). As shown in the figures, driving mechanism 96 is contained within handle 108. More specifically, mechanism 96 preferably includes a spring 102 housed in housing 104. Spring 102 is connected to lever 94 (via connecting hub 110) and crimping member 82, so that movement of lever 94 provides distal and proximal movement to crimping member 82. Spring member preferably keeps lever 94 and crimping member 82 in the relative positions shown in FIG. 11 and 6A, respectively. Thus, movement of the lever 94 as indicated by the arrow in FIG. 11 causes crimping member 82 to be forced against the staple for closure (crimping), as described above. Once crimped, a key hub 98 on the stapler is rotated to turn the shaft 86 approximately ninety degrees to align opening 74 of staple 70 with flange 84, as shown in FIG. 15. This permits disengagement of the staple 70 from the stapler 80, so that the stapler can be removed from the cannula, as shown in FIGS. 16 and 17. After the stapler is removed the stapled puncture site can be inspected (down the cannula) to ensure that the puncture site is correctly sealed (FIG. 19). In addition, the guide wire, if not previously removed, can be removed at this point. The vacuum is disengaged to permit the cannula to be removed from the incision in the skin, as shown in FIG. 18. It should be noted that other geometric configurations of the flange member and staple will necessitate an alternative rotation, which may be other than approximately 90 degrees.

The preferred material used for the construction of the devices shown in all the figures can include plastic, stainless steel, titanium, and bioabsorbable material (where appropriate).

Modifications to the present invention are also possible. For example, instead of a stapling device 80, as described above, an appropriate suturing mechanism, laser suturing mechanism, or other closure system can be used to seal the puncture site. In any event, the suction cannula 10 provides unobstructed access to the puncture site during medical procedures, including closure of the wound. The driving mechanism 96 of the stapler could be appropriately modified with a push-button activated gear mechanism to slide the crimping member distally. Those skilled in the art will recognize that many modifications are possible to drive the crimping member, and all such modifications are deemed within the scope of the present invention.

The shape of the staple 70/flange 84 can also be modified. For example, the member 76 can modified and shaped as a rectangle, triangle, square, etc. Alternatively, the member 76 can include a circular shape which is friction fit over the flange member. Accordingly, the flange 84 would be appropriately modified to match the opening 74 defined by the member 76 to permit engagement and disengagement of the staple 70 and flange 84, as described above. The staple 70 can be further modified with barbs on the prongs 72, to provide a more secure fastening of the staple to the artery wall. The crimping member 82 can be modified to include a conforming portion 90 having a variety of shapes, provided that the overall functionality of the crimping member, as described herein, is not hindered.

The vacuum source applied to the cannula 10 can be any conventionally known automated vacuum supply. Of course, the cannula can be appropriately modified to include a manually activated vacuum using, for example, a bulb mechanism, when a vacuum supply is otherwise unavailable.

Additional modifications are also possible. Referring to FIGS. 20–23, an alternative embodiment for the cannula and dilator are shown. In this embodiment, an outer sheath 110, preferably formed of plastic, is placed over the cannula 112 with the dilator 114 inserted into the cannula. The plastic sheath 110 is slidably engaged the over cannula using hub 120. As shown in FIGS. 21 and 23, the sheath 110 locks the distal tip 116 of the dilator 114 at juncture 118. Retracting the sheath 110 is accomplished by pulling proximally on hub 120, thereby opening the wing members 122 of the sheath 110. To that end, a latch 132 can be provided that holds the hub 120 in place. Preferably, latch 132 can be manually removed from the hub 120 to permit movement of the hub. Additionally, snap-fit interference locks 134a and 134b can be provided as shown to fix the hub (and sheath) in the proximal position, as indicated by the arrow. The cannula 112 may be of the type described above. Alternatively, instead of the tube-in-tube suction cannula set forth herein, the cannula can be modified so that only the distal tip 124 has a tube-in-tube construction. In other words, referring to FIGS. 1–3A, the tube-in-tube construction need not span the entire length of the device, but may rather only be provided at the tip section 124, recognizing that the stapler, dilator or other instruments will be inserted therein. The distal tip 116 of the dilator 114 is preferably constructed as shown in FIG. 23. Preferably, the distal tip can include a passage 126 in fluid communication with the dilator, to provide visual indication within the artery by the presence of blood (shown at the dilator hub section). It should be noted that the dilator tip can be elongated (more so than shown in the drawings) thereby reducing the angle of insertion into a vein or artery (as shown in FIG. 4A). Also alternatively, instead of a cannula having a tube-in-tube construction as described herein, the cannula 112 can modified to include only a single tube. In this case, the sheath 118 can replace the outer tube 18 of the cannula (FIG. 1) and a vacuum can be created within the space between the sheath and the cannula.

Figure 25B:
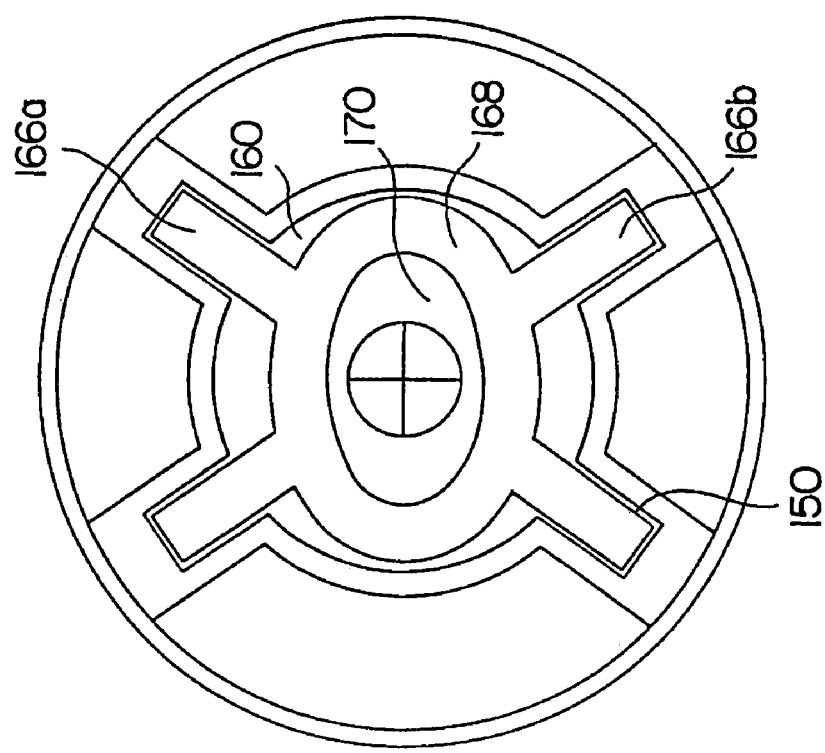
FIG. 25B depicts a cross-sectional view of the cannula of FIG. 25A, in cooperation with the stapler of FIGS. 24A and 24B.
Figure 25A:
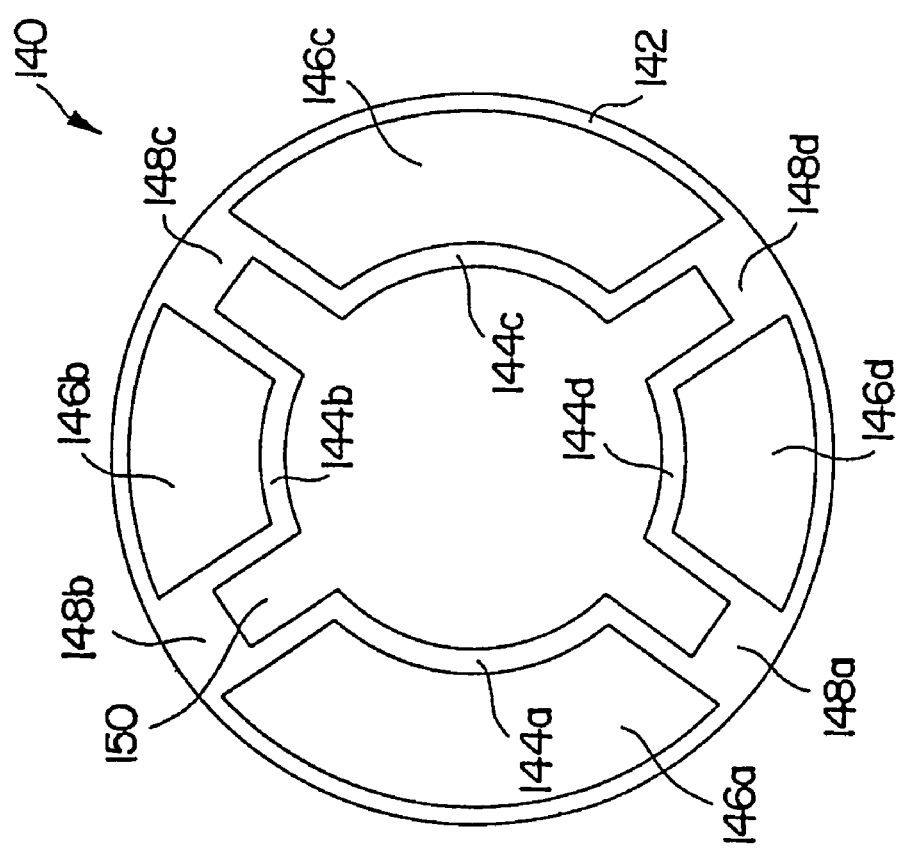
FIG. 25A depicts a cross-sectional view of another preferred cannula of the present invention.

Anther embodiment of the cannula 140 of the present invention is depicted in FIG. 25A. In this embodiment, an outer tube 142 is provided, similar to the embodiment of FIGS. 1–3A. The inner tube, however, is provided as a plurality of arcuate segments 144a–144d, connected to the outer tube by connecting members 148a–148d. The space between the segments 144a–d and the outer tube 142, shown as 146a–d, is preferably used for the vacuum, as described above. The connecting members 148a–d~caff also be constructed so as to provide a keyway space 150, which can be keyed to a variety of instruments, as will be described below. It should be noted that the construction shown in FIG. 25A can be extruded the entire length of the cannula 140, or provided at the distal tip thereof It should also be noted that the length of the arcuate segments and the positioning of the connecting members is a matter of design choice for a desired cross-sectional profile.

FIGS. 24A and 24B depict the tip section 160 of another preferred stapler of the present invention. In this embodiment, the tip section 160 includes a conforming portion 162 having a plurality of fingers 164a–d, which are located about the periphery of the section 160, and provided to urge the staple against the flange member (described above). The cooperation of the cannula of FIG. 25A and the stapler tip of FIGS. 24A and 24B is depicted in FIG. 25B. As shown in this figure, the space 150 permits passage therethrough of the stapler tip 160. Also shown in this drawing is the staple 168 and flange 170, which operate as described herein.

Although the detailed description provided herein has largely been in reference to arterial procedures, the present invention is not so limited. The cannula of the present invention can also be used in other tissue environments, as may be required.

What is claimed is:

1. A tissue stapler for deploying a staple into tissue, comprising a tubular member having a tip section, a trigger, and a connecting rod located within said tubular member and extending between said tip section and said trigger, a crimping member located on said tubular member and disposed within said tip section, said connecting rod having a flange member adapted to hold said staple between said flange member and said crimping member, said connecting rod and said tubular member being slidably operable by said trigger to slide said flange member toward said crimping member thereby deploying said staple.

2. A stapler as claimed in claim 1, wherein said connecting rod is rotatable within said tubular member, and said flange member is mated with an opening in said staple in one dimension, wherein said staple has an opening sized and shaped to be placed over said flange member and wherein, upon rotation of said connecting rod, said staple can be held against said crimping member by said flange member.

3. A stapler as claimed in claim 2, wherein said flange member has a generally oval shape and said opening in said staple has a mated oval shape.

4. A stapler as claimed in claim 1, wherein said trigger comprises a lever for moving said connecting rod within said tubular member.

5. A stapler as claimed in claim 1, wherein said staple comprises a plurality of tissue engaging prongs that are crimped together at least partially through said tissue by said crimping member.

6. A stapler as claimed in claim 1, wherein said crimping member has a generally parabolic shape.

7. A stapler as claimed in claim 1, wherein said crimping member has a plurality of slidable fingers, said crimping member being operable by said trigger to slide axially over said connecting rod and flange member to crimp said staple.

8. A staple and a stapler for stapling tissue, said stapler comprising a tubular member having a tip section, a trigger, and a connecting rod located within said tubular member and extending between said tip section and said trigger a crimping member located on said tubular member and disposed within said tip section, said connecting rod having a flange member adapted to hold said staple between said flange member and said crimping member, said connecting rod and said tubular member being slidably operable by said trigger to slide said flange member toward said crimping member thereby deploying said staple; and said staple comprising a ring member defining an opening therein, said opening being mated to fit over said flange member in one dimension and a plurality of tissue engaging members located on said ring member to pierce into tissue upon crimping by said stapler.

9. A staple and a stapler as claimed in claim 8, wherein said flange member and said opening have mated shapes.

10. A staple and a stapler as claimed in claim 8, wherein said connecting rod is rotatable within said tubular member, and said flange member is mated with an opening in said staple in one dimension, wherein said staple is adapted to be placed over said flange member and wherein, upon rotation of said connecting rod, said staple can be held against said crimping member by said flange member.

* * * * *